US009506092B2

(12) United States Patent
Dischert et al.

(10) Patent No.: US 9,506,092 B2
(45) Date of Patent: Nov. 29, 2016

(54) MICROORGANISM FOR METHIONINE PRODUCTION WITH ENHANCED GLUCOSE IMPORT

(75) Inventors: Wanda Dischert, Vic-le-Comte (FR); Rainer Figge, Le Crest (FR)

(73) Assignee: METABOLIC EXPLORER, Saint Beauzire (FR)

( * ) Notice: Subject to any disclaimer, the term of this patent is extended or adjusted under 35 U.S.C. 154(b) by 0 days.

(21) Appl. No.: 14/128,715

(22) PCT Filed: Jun. 29, 2012

(86) PCT No.: PCT/EP2012/062674
§ 371 (c)(1),
(2), (4) Date: Dec. 23, 2013

(87) PCT Pub. No.: WO2013/001055
PCT Pub. Date: Jan. 3, 2013

(65) Prior Publication Data
US 2014/0134680 A1 May 15, 2014

Related U.S. Application Data

(60) Provisional application No. 61/502,528, filed on Jun. 29, 2011.

(30) Foreign Application Priority Data

Jun. 29, 2011 (EP) ..................................... 11305829

(51) Int. Cl.
C12P 13/12 (2006.01)
C07K 14/245 (2006.01)
C12N 9/12 (2006.01)

(52) U.S. Cl.
CPC .............. *C12P 13/12* (2013.01); *C07K 14/245* (2013.01); *C12N 9/1205* (2013.01); *Y02P 20/52* (2015.11)

(58) Field of Classification Search
None
See application file for complete search history.

(56) References Cited

U.S. PATENT DOCUMENTS

| 7,611,873 B1 | 11/2009 | Usuda et al. |
| 7,790,424 B2 | 9/2010 | Park et al. |
| 2004/0229320 A1 | 11/2004 | Stoynova et al. |
| 2006/0270013 A1 | 11/2006 | Chateau et al. |

FOREIGN PATENT DOCUMENTS

| EP | 2 314 710 A2 | 4/2011 |
| EP | 2 573 189 A1 | 3/2013 |
| JP | 2000-157267 A | 6/2000 |
| JP | 2009-521939 A | 6/2009 |
| JP | 2010-539962 A | 12/2010 |
| WO | 02/10209 | 2/2002 |
| WO | 02/081721 | 10/2002 |
| WO | 03/004670 | 1/2003 |
| WO | 03/004675 | 1/2003 |
| WO | WO-2004076659 A2 | 9/2004 |
| WO | WO-2004076659 A3 | 9/2004 |
| WO | 2005/059093 | 6/2005 |
| WO | 2006/001616 | 1/2006 |
| WO | 2006/008097 | 1/2006 |
| WO | WO-2007119576 A1 | 10/2007 |
| WO | 2009/078687 | 6/2009 |
| WO | 2010/020681 A1 | 2/2010 |
| WO | WO-2012055798 A1 | 5/2012 |
| WO | WO 2012/090021 | * 7/2012 |

OTHER PUBLICATIONS

International Search Report for PCT/EP2012/062674 Mailed Sep. 20, 2012.
"European Application Serial No. 151305829, Search Report mailed Jan. 31, 2012", 5 pgs.
Anderson, E H, "Growth Requirements of Virus-Resistant Mutants of *Escherichia coli* Strain "B"", Proc Natl Acad Sci USA. 32(5), (May 1946), 120-128.
Baba, Tomoya, et al., "Construction of *Escherichia coli* K-12 in-frame single-gene knockout mutant: the Keio collection", Molecular Systems Biology 2, doi: 10.1038/msb4100050, (2006), 1-11.
Datsenko, Kirill A, et al., "One-stem inactivation of chromosomal genes in *Escherichia coli* K-12 using PCR products", PNAS 97(12), (Jun. 2000), 6640-6645.
Dennis, Jonathan J, et al., "Plasposons: Modular Self-Cloning Minitransposon Derivatives for Rapid Genetic Analysis of Gram-Negative Bacterial Genomes", Applied and environmental Microbiology 64(7), (Jul. 1998), 2710-2715.
Giladi, Hilla, et al., "Enhanced activity of the bacteriophage lambda PL promoter at low temperature", FEMS Microbiol Rev. 17, (Aug 1995), 135-40.

(Continued)

*Primary Examiner* — Nashaat Nashed
(74) *Attorney, Agent, or Firm* — Birch, Stewart, Kolasch & Birch, LLP

(57) ABSTRACT

The present invention is related to a recombinant microorganism for improved methionine production comprising modifications to produce methionine from glucose as main carbon source by fermentation, and modifications to improve glucose import, wherein the glucose import is improved by modifying the expression of at least one gene selected from ptsG, sgrT sgrS and dgsA.

The invention is also related to a method for the fermentative production of methionine or methionine derivatives comprising the steps of:

culturing the recombinant microorganism as described above in an appropriate culture medium comprising a fermentable source of carbon containing glucose and a source of sulphur, and recovering methionine or methionine derivatives from the culture medium.

16 Claims, 1 Drawing Sheet

(56) References Cited

OTHER PUBLICATIONS

Görke, Boris, et al., "Noncoding RNA Control of the making and breaking of sugars", Genes Dev. 22(21), doi: 0.1101/gad.1717808, (Nov. 2008), 2914-25.
Harrington, K J, et al., "Balanced branching in transcription termination", PNAS 98(9), (Apr. 2001), 5019-2054.
Kadner, Robert J, et al., "Two mechanisms for growth inhibition by elevated transport of sugar phosphate in *Escherichia coli*", Journal of General Microbiology 138, (1992), 2007-2014.
Kimata, Keiko, et al., "A global repressor (Mlc) is involved in glucose induction of the ptsG gene encoding major glucose transporter in *Escherichia coli*", Mol Microbiol. 29(6), (Sep. 1998), 1509-19.
Kincade, Julie, et al., "Bacteriophage lambda promoters pL and pR: sequence determinants of in vivo activity and of sensitivity to the DNA gyrase inhibitor, coumermycin", Gene. 97(1), (Jan. 1991), 7-12.
Kornberg, H L, et al., "Inducible phosphoenolpyruvate-dependent hexose phosphotransferase activities in *Escherichia coli*", Biochem J. 128(5), (Aug. 1972), 1339-44.
Lee, Annette T, et al., "Elevated glucose 6-phosphate levels are associated with plasmid mutations in vivo", Proc. Natl. Acad. Sci. USA 84, (Dec. 1987), 8311-8314.
Lee, Sung-Jae, et al., "Signal transduction between a membrane-bound transporter, PtsG, and a soluble transcription factor, Mlc, of *Escherichia coli*", the EMBO Journal 19(20), (2000), 5353-5361.
Meadow, Norman D, et al., "The Bacterial Phosphoenol-Pyruvate: Glycose Phosphotransferase System", Annual Review of Biochemistry 59, DOI: 10.1146/annurev.bi.59.070190.002433, (1990), 497-542.
Meynial-Salles, Isabelle, et al., "New Tool for Metabolic Pathway Engineering in *Escherichia coli*: One-Step Method to Modulate Expression of Chromosomal Genes", Applied and Environmental Microbiology 71(4), (Apr. 2005), 2140-2144.
Morita, Teppei, et al., "Smal RNAs making a small protein", PNAS 104(51), (Dec. 2007), 20149-20150.
Negrete, Alejandro, et al., "Glucose uptake regulation in *E. coli* by the small RNA SgrS: comparative analysis of *E. coli* K-12 (JM109 and MG1655) and *E. coli* B (BL21)", Microb Cell Fact. 9(1), doi: 10.1186/1475-2859-9-75, (Sep. 2010), 75.
Orosz, Andras, et al., "Analysis of the complex transcription termination region of the *Escherichia coli* rrnB gene", Eur. J. Biochem. 201, (1991), 653-659.
Plumbridge, Jacqueline, "Expression of ptsG, the gene for the major glucose PTS transporter in *Escherichia coli*, is repressed by Mlc and induced by growth on glucose", Mol Microbiol. 29(4), (Aug. 1998), 1053-63.
Plumbridge, Jacqueline, "Regulation of gene expression in the PTS in *Escherichia coli*: the role and interactions of Mlc", Curr Opin Microbiol. 5(2), (Apr. 2002), 187-93.
Rohwer, Johann, et al., "Changes in the cellular energy state affect the activity of the bacterial phosphotransferase system", Eur. J. Biochem. 235, (1996), 225-230.
Rungrassamee, W., et al., "Activation of glucose transport under oxidative stress in *Escherichia coli*", Arch Microbiol 190, (2008), 41-49.
Saunderson, C Linda, et al., "Comparative metabolism of L-methionine, DL-methionine and DL-2-hydroxy 4-methylthiobutanoic acid by broiler chicks", British Journal of Nutrition 54, (1985), 621-633.
Tanaka, Yuya, et al., "Negative regulation of the pts operon by Mlc: mechanism underlying glucose induction in *Escherichia coli*", Genes to Cells 4, (1999), 391-399.
Tchieu, Jason H, et al., "The Complete Phosphotranserase System in *Escherichia coli*", J. Mol Microbiol. Biotechnol. 3(3), (2001), 329-349.
Wadler, Caryn S, et al., "A dual function for a bacterial small RNA: SgrS performs base pairing-dependent regulation and encodes a functional polypeptide", PNAS 104(51), (2007), 20454-20459.
Zeppenfeld, Tim, et al., "Glucose Transporter Mutants of *Escherichia coli* K-12 with Changes in Substrate Recognition of IICB-GLC and Induction Behavior of the ptsG Gene", Journal of Bacteriology 182(16), (Aug. 2000), 4443-4452.
Usuda et al., "Effects of Deregulation of Methionine Biosynthesis on Methionine Excretion in *Escherichia coli*" Applied and Environmental Microbiology. (2005) vol. 71, No. 6: 3228-3234.
Lee et al., "Multimetaboilite Control of a Biosynthetic Pathway by Sequential Metabolites" The Journal of Biological Chemistry. (1966) vol. 241, No. 22: 5479-5480.
Lawrence, David A., "Regulation of the Methionine Feedback Sensitive Enzyme in Mutants of *Salmonella typhimurium*," Journal of Bacteriology. (1972) vol. 109, No. 1: 8-11.
Chater et al., "A Genetical Study of he Feedback-sensitive Enzyme of Methionine Synthesis in *Salmonella typhimurium*" Journal of General Microbiology. (1970) vol. 63: 111-120.
Omori et al., "Role of Serine 352 in the Allosteric Response of Serratia marcescens Aspartokinase I-Homoserine Dehydrogenase I Analyzed by Using Site-Directed Mutagenesis" Journal of Bacteriology. (1993) vol. 175, No. 4: 959-965.
Patte et al., Biochim. Biophys. Acta. (1966) vol. 128: 426-439.
PCT Form PCT/RO/132 dated Feb. 15, 2011, issued in counterpart International Application No. PCT/IB2010/003515.

* cited by examiner

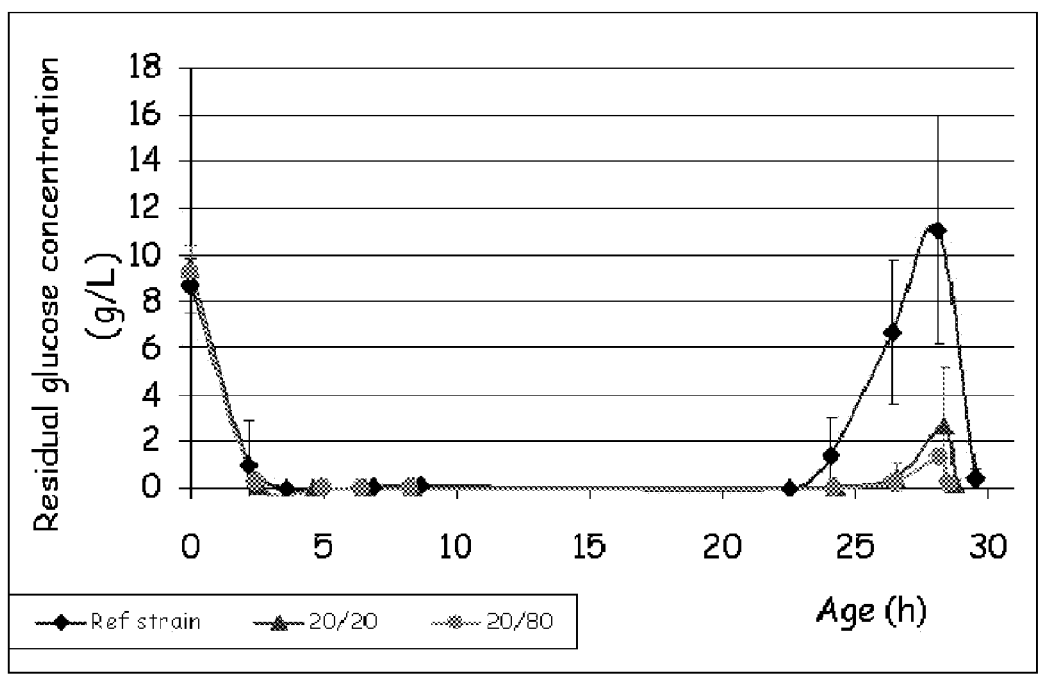

MICROORGANISM FOR METHIONINE PRODUCTION WITH ENHANCED GLUCOSE IMPORT

CROSS REFERENCE TO RELATED APPLICATIONS

This application is a §371 National Stage Application of PCT/EP2012/062674, filed Jun. 29, 2012, which claims priority to European Application No. 11305829.1, filed Jun. 29, 2011, and claims benefit of U.S. Provisional Application No. 61/502,528, filed Jun. 29, 2011.

BACKGROUND OF THE INVENTION

Field of the Invention

The present invention relates to an improved microorganism for the production of methionine and process for the preparation of methionine. In particular, the present invention relates to a microorganism for methionine production with improved glucose import comprising modified expression of at least one gene selected from ptsG, sgrS, sgrT or dgsA.

Description of Related Art

Sulphur-containing compounds such as cysteine, homocysteine, methionine or S-adenosylmethionine are critical to cellular metabolism and are produced industrially to be used as food or feed additives and pharmaceuticals. In particular methionine, an essential amino acid, which cannot be synthesized by animals, plays an important role in many body functions. Aside from its role in protein biosynthesis, methionine is involved in transmethylation and in the bioavailability of selenium and zinc. Methionine is also directly used as a treatment for disorders like allergy and rheumatic fever. Nevertheless, most of the methionine that is produced is added to animal feed.

With the decreased use of animal-derived proteins as a result of BSE and chicken flu, the demand for pure methionine has increased. Commonly, D,L-methionine is produced chemically from acrolein, methyl mercaptan and hydrogen cyanide. However, the racemic mixture does not perform as well as pure L-methionine (Saunderson, C. L., 1985). Additionally, although pure L-methionine can be produced from racemic methionine, for example, through the acylase treatment of N-acetyl-D,L-methionine, this dramatically increases production costs. Accordingly, the increasing demand for pure L-methionine coupled with environmental concerns render microbial production of methionine an attractive prospect.

Optimising the production of a chemical from a microorganism typically involves overexpressing proteins involved in the biosynthesis pathway, attenuating proteins involved in repression of the biosynthesis pathway or attenuating proteins involved in the production of undesirable by-products. All these approaches for the optimisation of L-methionine production in microorganisms have been described previously (see, for example, U.S. Pat. No. 7,790,424, U.S. Pat. No. 7,611,873, patent applications WO 2002/10209, WO 2006/008097 and WO 2005/059093); however, industrial production of L-methionine from microorganisms requires further improvements.

Typically, L-methionine has been produced by microorganisms grown on glucose as a main carbon source in a fermentative process. In bacteria, external glucose is transported into the cell and phosphorylated by the phosphoenolpyruvate: sugar phosphotransferase system (PTS) (Meadow et al. 1990; Rohwer et al. 1996; Tchieu et al. 2001). The PTS consists of two common cytoplasmic proteins, enzyme I and HPr, and a series of sugar-specific enzyme II complexes (EIIs). The PTS enzyme IICB$^{Glc}$, encoded by ptsG in $E.\ coli$ transports and concomitantly phosphorylates glucose to glucose-6-phosphate (G6P). While G6P is an essential intermediate in glucose metabolism, its intracellular accumulation causes the phenomenon of sugar-phosphate toxicity, also called "phosphosugar stress". Indeed, the accumulation of glucose has been reported to be very toxic for bacteria, giving rise to glycation, DNA mutagenesis and growth inhibition (Lee and Cerami, 1987; Kadner et al. 1992).

Recent studies have demonstrated that in $E.\ coli$ the ptsG gene encoding IICB$^{Glc}$ is highly regulated in quite an intriguing manner at both the transcriptional and post-transcriptional level, depending on physiological conditions (Plumbridge, 1998; Kimata et al. 1998; Plumbridge et al. 2002; Morita and Aïba, 2007; Görke and Vogel, 2008). Specifically, several levels of regulation have been identified:

regulation of the expression of ptsG gene by many different regulators (ArcA, Fis, Crp) and in particular the repression by DgsA, a transcriptional regulator firstly called Mlc (Making larger colonies);

destabilization of the ptsG mRNA by the small RNA sgrS (Sugar transport-related sRNA) by an antisense mechanism;

control of PtsG activity by the small polypeptide SgrT by a yet unknown mechanism; and regulation of the expression of sgrS/sgrT by the transcriptional regulator SgrR.

Due to the toxicity of G6P and the highly regulated and complex nature of the system, manipulation of the glucose transport system in microorganisms is very difficult. To date there have been several attempts to improve amino acids production and in particular threonine production by increasing glucose import by manipulating ptsG or dgsA genes (WO03004675 and WO03004670 of Degussa; US2004229320 of Ajinomoto and WO0281721 of Degussa). Nevertheless, there is no example of improving the production of methionine by increasing the glucose import of the bacterium.

SUMMARY

The inventors of the present invention have overcome the difficulties discussed above to improve L-methionine production by a microorganism through increasing glucose import. Accordingly, in a first aspect, the present invention provides a recombinant microorganism for improved methionine production comprising: a) modifications to produce methionine from glucose as main carbon source by fermentation, and b) modifications to improve glucose import, wherein glucose import is improved by modifying the expression of at least one gene selected from ptsG, sgrT, sgrS or dgsA (mlc).

The inventors show that by modifying the expression of the genes involved in the import of glucose, the glucose import into the microorganism is improved and the production of methionine by the microorganism is increased. Further, the inventors have found that modifying the expression of the genes involved in the import of glucose decreases the production of by-products ketomethylvalerate (KMV) and homolanthionine (HLA), thus improving the purity of the product methionine. In one embodiment, expression of the gene ptsG encoding IICB$^{Glc}$ is enhanced. While the expression of ptsG may be enhanced by any means known in the art, in one embodiment, the gene ptsG is overexpressed under the control of an inducible or a constitutive promoter. In another embodiment, the gene ptsG does not contain the sequence of the binding site for the small RNA sgrS.

In other embodiments, expression of the gene sgrS, sgrT or dgsA is attenuated. Methods of attenuating gene expression are well known to those skilled in the art. In one embodiment, the gene sgrS is deleted. In another embodiment, the gene sgrT is deleted. In a further embodiment of the invention the gene dgsA is deleted.

Further, glucose import may be improved through a combination of the above discussed modifications. In one embodiment, expression of the gene ptsG is enhanced and expression of the gene sgrS is attenuated. In another embodiment, expression of the gene ptsG is enhanced and expression of the gene sgrT is attenuated. In a further embodiment, expression of the gene ptsG is enhanced and expression of the genes sgrS and sgrT are attenuated. In another embodiment, expression of the gene ptsG is enhanced and expression of the gene dgsA is attenuated.

The microorganism of the present invention is modified to produce methionine. While it will be understood that the microorganism may comprise any modification known in the art to promote the production of methionine in a microorganism, in one embodiment, the expression of at least one of the following genes is enhanced: pyc, pntAB, cysP, cysU, cysW, cysA, cysM, cysJ, cysI, cysH, gcvT, gcvH, gcvP, lpd, serA, serB, serC, cysE, metF, metH, thrA, a metA allele encoding for an enzyme with reduced feed-back sensitivity to S-adenosylmethionine and/or methionine (MetA*), or a thrA allele encoding for an enzyme with reduced feed-back inhibition to threonine (thrA*). In one embodiment, at least one gene is under the control of an inducible promoter. In another embodiment, the expression of at least one of the following genes is attenuated: metJ, pykA, pykF, purU, yncA, or udhA.

In a particularly preferred embodiment, the expression of the gene metJ is attenuated. In another embodiment, the expression of the gene metJ is attenuated and the expression of a metA allele encoding for an enzyme with reduced feed-back sensitivity to S-adenosylmethionine and/or methionine (MetA*) is enhanced. In a further embodiment, the expression of the gene metJ is attenuated; the expression of a metA allele encoding for an enzyme with reduced feed-back sensitivity to S-adenosylmethionine and/or methionine (MetA*) is enhanced; and the expression of a thrA allele encoding for an enzyme with reduced feed-back inhibition to threonine (thrA*) is enhanced. In yet another embodiment, the expression of the gene metJ is attenuated; the expression of a metA allele encoding for an enzyme with reduced feed-back sensitivity to S-adenosylmethionine and/or methionine (MetA*) is enhanced; the expression of a thrA allele encoding for an enzyme with reduced feed-back inhibition to threonine (thrA*) is enhanced; and the expression of the gene cysE is enhanced. In still a further embodiment, the expression of the gene metJ is attenuated; the expression of a metA allele encoding for an enzyme with reduced feed-back sensitivity to S-adenosylmethionine and/or methionine (MetA*) is enhanced; the expression of a thrA allele encoding for an enzyme with reduced feed-back inhibition to threonine (thrA*) is enhanced; the expression of the gene cysE is enhanced; and the expression of the genes metF and/or metH is enhanced. In a particular embodiment, the present invention comprises a microorganism wherein: a) the gene pstG is overexpressed and/or does not contain the sRNA sgrS binding site and/or the gene sgrS is deleted and/or the gene sgrT is deleted and/or the gene dgsA is deleted; b) the expression of the genes metA*, metH, cysPUWAM, cysJIH, gcvTHP, metF, serA, serB, serC, cysE, thrA* and pyc are enhanced; and c) the expression of the genes metJ, pykA, pykF, purU and yncA are attenuated.

The microorganism of the present invention produces less ketomethylvalerate (KMV) and homolanthionine (HLA) and as such produces methionine of improved purity. In one embodiment, the methionine produced has increased purity. In one embodiment, there is provided a method for the fermentative production of methionine of increased purity comprising the steps of: a) culturing the recombinant microorganism described above in an appropriate culture medium comprising a fermentable source of carbon containing glucose and a source of sulphur, and b) recovering methionine or methionine derivatives from the culture medium.

In a second aspect, the present invention provides a method for the fermentative production of methionine of increased purity comprising the steps of: a) culturing the recombinant microorganism in an appropriate culture medium comprising a fermentable source of carbon containing glucose and a source of sulphur, wherein said microorganism comprises: i) modifications to produce methionine from glucose as main carbon source by fermentation, and ii) modifications to improve glucose import, wherein glucose import is improved by modifying the expression of at least one gene selected from ptsG, sgrT, sgrS or dgsA, and b) recovering methionine or methionine derivatives from the culture medium.

It will be appreciated that the present invention also relates to a method of producing methionine or methionine derivatives. In one embodiment, there is provided a method for the fermentative production of methionine or methionine derivatives comprising the steps of: a) culturing the recombinant microorganism described above in an appropriate culture medium comprising a fermentable source of carbon containing glucose and a source of sulphur, and b) recovering methionine or methionine derivatives from the culture medium.

In a third aspect, the present invention provides a method for the fermentative production of methionine or methionine derivatives comprising the steps of: a) culturing the recombinant microorganism in an appropriate culture medium comprising a fermentable source of carbon containing glucose and a source of sulphur, wherein said microorganism comprises: i) modifications to produce methionine from glucose as main carbon source by fermentation, and ii) modifications to improve glucose import, wherein glucose import is improved by modifying the expression of at least one gene selected from ptsG, sgrT, sgrS or dgsA and b) recovering methionine or methionine derivatives from the culture medium.

BRIEF DESCRIPTION OF THE DRAWING

FIG. 1 represents embodiments as described herein.

DETAILED DESCRIPTION OF A PREFERRED EMBODIMENT

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting, which will be limited only by the appended claims.

All publications, patents and patent applications cited herein, whether supra or infra, are hereby incorporated by reference in their entirety. However, publications mentioned herein are cited for the purpose of describing and disclosing the protocols, reagents and vectors which are reported in the publications and which might be used in connection with the invention. Nothing herein is to be construed as an admission that the invention is not entitled to antedate such disclosure by virtue of prior invention.

Furthermore, the practice of the present invention employs, unless otherwise indicated, conventional microbiological and molecular biological techniques within the skill of the art. Such techniques are well known to the skilled worker, and are explained fully in the literature. See, for example, Prescott et al. (1999); and Sambrook et al., (1989) (2001).

It must be noted that as used herein and in the appended claims, the singular forms "a", "an", and "the" include plural reference unless the context clearly dictates otherwise. Thus, for example, a reference to "a microorganism" includes a plurality of such microorganisms, and a reference to "an enzyme" is a reference to one or more enzymes, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

As used herein, the following terms may be used for interpretation of the claims and specification.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

In the description of the present invention, genes and proteins are identified using the denominations of the corresponding genes in *E. coli*. However, and unless specified otherwise, use of these denominations has a more general meaning according to the invention and covers all the corresponding genes and proteins in other organisms, more particularly microorganisms.

PFAM (protein families database of alignments and hidden Markov models; that can be used on the Wellcome Trust Sanger Institute website, represents a large collection of protein sequence alignments. Each PFAM makes it possible to visualize multiple alignments, see protein domains, evaluate distribution among organisms, gain access to other databases, and visualize known protein structures.

COGs (clusters of orthologous groups of proteins) that can be used on the National Center for Biotechnology Information website, are obtained by comparing protein sequences from 66 fully sequenced genomes representing 38 major phylogenic lines. Each COG is defined from at least three lines, which permits the identification of former conserved domains.

The means of identifying homologous sequences and their percentage homologies are well known to those skilled in the art, and include in particular the BLAST programs, which can be used from the National Center for Biotechnology Information website with the default parameters indicated on that website. The sequences obtained can then be exploited (e.g., aligned) using, for example, the programs CLUSTALW, that can be used on the European Bioinformatics Institute website or MULTALIN, that can be used on the MultAlin website, with the default parameters indicated on those websites.

Using the references given on GenBank for known genes, those skilled in the art are able to determine the equivalent genes in other organisms, bacterial strains, yeasts, fungi, mammals, plants, etc. This routine work is advantageously done using consensus sequences that can be determined by carrying out sequence alignments with genes derived from other microorganisms, and designing degenerate probes to clone the corresponding gene in another organism. These routine methods of molecular biology are well known to those skilled in the art, and are claimed, for example, in Sambrook et al. (1989).

The present invention relates to a recombinant microorganism for methionine production. Specifically, the present invention relates to improving methionine production in a microorganism by increasing glucose import.

The term "improved methionine production" refers to an increased productivity of methionine and/or an increased titer of methionine and/or an increased methionine/carbon source yield and/or an increased purity of methionine. The term "increased methionine/carbon source yield" defines the quantity of methionine obtained during the fermentation divided by the quantity of glucose that has been consumed. It can be expressed in percent g methionine/g glucose or mol methionine/mol glucose. The term "increased" in this context describes a measurable increase compared to the microorganism without the specified modifications. In preferred embodiments, the increase is of at least about 7%, preferentially at least about 15%, preferentially at least about 25%, most preferentially at least about 30%. The total methionine/glucose yield is preferentially at least about 7% g/g, preferentially at least about 15% g/g, preferentially at least about 20% g/g, most preferentially at least about 24% g/g.

Methods for determining the amount of glucose consumed and methionine produced are well known to those in the art and are discussed elsewhere herein.

The terms "increased purity of methionine" or "methionine of increased purity" relate to the quantity of ketomethylvalerate (KMV) and/or homolanthionine (HLA) obtained during the fermentation compared to the quantity of methionine produced. In this context, the ratio of the amount of KMV and HLA compared to the amount of methionine is improved in the microorganism of the invention. This ratio may be improved either by decreasing the quantity of KLV and HLA produced or by improving the quantity of methionine produced while concentration of KMV and HLA remains constant or both. Advantageously, it refers also to the quantity of glucose remaining in the fermentation broth at the end of the culture compared to the quantity of methionine produced. In this invention, the ratio of glucose remaining in the fermentation broth compared to the amount of produced methionine is decreased in the microorganism of the invention. This ratio may be improved either by decreasing the quantity of glucose remaining in the fermentation broth or by improving the quantity of methionine produced while the total amount of glucose injected in the fermentor remains constant or both.

Methods for determining the amount of methionine, NAM, KMV, HLA and glucose contained in the medium are well known to those skilled in the art. For example, the amount of L_methionine may be measured by HPLC after OPA/Fmoc derivatization using L-methionine (Fluka, Ref 64319) as a standard.

As discussed above, external glucose is transported into bacteria cells and phosphorylated by the phosphoenolpyruvate: sugar phosphotransferase system (PTS) (Meadow et al. 1990; Rohwer et al. 1996; Tchieu et al. 2001). Phosphorylated glucose is toxic to cells in high concentrations and as such the PTS system is highly regulated. This, coupled with the fact that the system is complex, makes manipulation of the system very difficult. However, as described below, the present inventors have produced a recombinant microorganism with improved glucose import.

The term "recombinant microorganism", as used herein, refers to a bacterium, yeast or a fungus that is not found in nature and is genetically different from equivalent microorganisms found in nature. According to the invention, the term "modifications" designate any genetic change introduced or induced in the microorganism. The microorganism may be modified through either the introduction or deletion of new genetic elements. Further, a microorganism may be modified by forcing the development and evolution of new metabolic pathways by combining directed mutagenesis and evolution under specific selection pressure (see, for example, WO 2004/076659). Preferentially, the microorganism is selected from the group comprising Enterobacteriaceae, Clostridiaceae, Bacillaceae, Streptomycetaceae, Corynebacteriaceae and Saccharomyceteceae. More preferentially the microorganism is a species of Enterobacteriaceae or Corynebacteriaceae or *Saccharomyces cerevisiae*. In one embodiment, the microorganism is *Escherichia coli* (*E. coli*).

In particular, the examples show modified *E. coli* strains, but these modifications can easily be performed on other microorganisms of the same family.

*E. coli* belongs to the Enterobacteriaceae family which comprises members that are Gram-negative, rod-shaped, non-spore forming and are typically 1-5 μm in length. Most members have flagella used to move about, but a few genera are non-motile. Many members of this family are a normal part of the gut flora found in the intestines of humans and other animals, while others are found in water or soil, or are parasites on a variety of different animals and plants. *E. coli* is one of the most important model organisms, but other important members of the Enterobacteriaceae family include *Klebsiella*, in particular *Klebsiella pneumoniae*, and *Salmonella*.

The term "improve glucose import", "improved glucose import", and grammatical equivalents thereof, as used herein, refers to an increased glucose uptake rate. The term "increased glucose uptake rate" refers to the quantity of glucose consumed during the fermentation divided by the biomass concentration. Specifically, glucose uptake rate can be defined as described below:

$$qS = \frac{r_S}{X},$$

where $r_s$ is the glucose uptake rate and X the biomass concentration.

The glucose uptake rate can be described as:

$$r_S = \frac{dS}{dt},$$

where S is the quantity of glucose consumed at time t. For fed batch fermentation, the amount glucose consumed during the culture corresponds to the glucose present in the batch culture plus the glucose added in the inoculum plus the glucose injected during the fed batch phase minus the residual glucose at the end of the experiment is subtracted. Other techniques can be used and are described in the literature:

The use of the fluorescent glucose analog (2-(N-(7-nitrobenz-2-oxa-1,3-diazol-4-yl)amino)-2-deoxyglucose or 2-NBDG) to measure rates of glucoses uptake (Natarajan A. and Srienc F. (1999) metabolic engineering, vol 1, issue 4, 320-333), Measurement of the PtsG activity (Kornberg H. L. and Reeves R. E. Biochem. J. (1972) 128, 1339-1344; Rungrassamee et al., Erch Microbiol (2008) 190:41-49), qRT-PCR (quantitative real time polymerase chain reaction) profiling which is used to quantify a specific target like ptsG mRNA and confirm an enhanced expression of the corresponding gene.

The term "increased" in this context describes a measurable increase compared to the microorganism without the specified modifications.

According to the present invention, glucose import is improved by modifying the expression of at least one gene selected from ptsG, sgrT, sgrS or dgsA. Moreover, the improvement of the glucose import by the overexpression of ptsG or via an increased activity of PtsG in the microorganism can be measured by different techniques known by the man skilled in the art.

The term "modifying the expression", as used herein, indicates that expression of a gene is increased or decreased through the introduction or deletion of genetic elements. Typically, expression of the gene is increased or decreased in comparison to an equivalent microorganism that has not been modified, ie. a microorganism that does not comprise the introduction or deletion of genetic elements to improve glucose transport. Methods of determining whether the expression of a gene is increased or decreased in reference to a standard are well known in the art and are also discussed infra.

Glucose import is improved according to the present invention by enhancing the expression of the gene ptsG. The ptsG gene encodes the PTS enzyme IICB$^{Glc}$ (synonyms-EC 2.7.1.69; protein-N(pi)-phosphohistidine-sugar phosphotransferase; enzyme II of the phosphotransferase system;

PEP-sugar phosphotransferase enzyme II; PTS permease) in *E. coli*. The nucleotide sequence of the ptsG gene is shown in SEQ ID NO: 18.

The term "enhanced", "enhance", and grammatical equivalents thereof, as used herein, refers to a modification that increases or up-regulates the expression of a gene compared to an equivalent microorganism that has not been modified. The terms "enhanced expression", "increased expression" or "overexpression" are used interchangeably in the text and have similar meaning.

Various means of increasing the expression of a gene in a microorganism are known to those skilled in the art and include, for example, increasing the stability of the messenger RNA, increasing the number of copies of the gene, using a stronger promoter, removing regulatory elements or using an allele with increased activity, or possibly by combining these measures. Further, the expression of a gene may be increased through chromosomal or extra chromosomal means. For example, several copies of the gene may be introduced into the genome of the microorganism by recombination methods. Alternatively, genes may be carried by different types of plasmids that differ with respect to their origin of replication and thus their copy number in the cell. Genes may be present in 1-5 copies, about 20 or up to 500 copies, corresponding to low copy number plasmids with tight replication (pSC101, RK2), low copy number plasmids (pACYC, pRSF1010) or high copy number plasmids (pSK bluescript II). Regulatory elements are important for controlling the expression of genes. For example, genes may be expressed using promoters of different strengths, which, in addition, may be inducible. These promoters may be homologous or heterologous. It is well within the ability of the person skilled in the art to select appropriate promoters; however, for example, the promoters Ptrc, Ptac, Plac or the lambda promoter cI are widely used. In one embodiment, expression of the gene ptsG is enhanced by placing the gene under the control of an inducible or a constitutive promoter.

In another embodiment, expression of the gene ptsG is enhanced by removing the sequence coding for the binding site of the small RNA sgrS.

The term "removing the sequence coding for the binding site of the small RNA sgrS" means that the binding site of the small RNA sgrS (SEQ ID NO: 19) is deleted totally or partially so as to prevent the binding of small RNA sgrS on the gene ptsG.

Glucose import is also improved by attenuating the expression of the gene sgrS and/or the gene sgrT and/or the gene dgsA. The sgrS gene encodes the small RNA Sugar transport-related sRNA in *E. coli*. The nucleotide sequence of the sgrS gene is shown in SEQ ID NO: 20. The sgrT gene encodes the small polypeptide SgrT in *E. coli*. The nucleotide sequence of the sgrT gene is shown in SEQ ID NO: 21. The dgsA gene encodes a global regulator acting as a transcriptional repressor for several genes especially ptsG gene and ptsHIcrr operon from *E. coli*. The nucleotide sequence of the dgsA gene is shown in SEQ ID NO: 22.

The term "attenuated", as used herein, refers to the partial or complete suppression of the expression of a gene. This suppression of expression can be either an inhibition of the expression of the gene, a deletion of all or part of the promoter region necessary for expression of the gene, a deletion in the coding region of the gene, and/or the exchange of the wild-type promoter for a weaker natural or synthetic promoter. Preferentially, the attenuation of a gene is essentially the complete deletion of that gene, which can be replaced by a selection marker gene that facilitates the identification, isolation and purification of the strains according to the invention. For example, suppression of gene expression may be achieved by the technique of homologous recombination (Datsenko & Wanner, 2000). In one embodiment, glucose import is improved by deletion of the gene sgrS. In another embodiment, glucose import is improved by deletion of the gene sgrT. In another embodiment, glucose import is improved by deletion of the gene dgsA.

In a further embodiment, glucose import is improved through a combination of the above discussed modifications. For example, in the microorganism of the invention glucose import may be improved by:

enhancing the expression of the gene ptsG and attenuating the expression of the gene sgrS;

enhancing the expression of the gene ptsG and attenuating the expression of the gene sgrT;

enhancing the expression of the gene ptsG and attenuating the expression of the gene dgsA;

enhancing the expression of the gene ptsG and attenuating the expression of the gene sgrS and the gene sgrT, enhancing the expression of the gene ptsG and attenuating the expression of the gene dgsA and the gene sgrS, enhancing the expression of the gene ptsG and attenuating the expression of the gene dgsA and the gene sgrT, enhancing the expression of the gene ptsG and attenuating the expression of the gene dgsA and the genes sgrT and sgrS, attenuating the expression of the gene dgsA and attenuating the expression of the genes sgrS and/or sgrT.

In a preferred embodiment of the invention, glucose import is improved by enhancing the expression of the gene ptsG and attenuating the expression of the gene sgrS and the gene sgrT.

In another preferred embodiment of the invention, glucose import is improved by enhancing the expression of the gene ptsG and attenuating the expression of the gene dgsA.

More preferably, glucose import is improved by enhancing the expression of the gene ptsG and attenuating the expression of the gene dgsA and the genes sgrT and sgrS.

The modifications to improve glucose transport in order to improve methionine production are not made in isolation, but in combination with modifications that promote the fermentative production of methionine by a microorganism from glucose as a main carbon source. Modifications that promote the production of methionine in a microorganism are well known to those skilled in the art. In one embodiment, the expression of at least one of the following genes is enhanced: pyc, pntAB, cysP, cysU, cysW, cysA, cysM, cysJ, cysI, cysH, gcvT, gcvH, gcvP, lpd, serA, serB, serC, cysE, metF, metH, thrA, a metA allele encoding for an enzyme with reduced feed-back sensitivity to S-adenosyl-methionine and/or methionine (MetA*), or a thrA allele encoding for an enzyme with reduced feed-back inhibition to threonine (thrA*). In a particular embodiment of the invention at least one of these genes may be under the control of an inducible promoter. In a preferred embodiment of the invention the gene thrA* is expressed under an inducible promoter.

In another embodiment, the expression of at least one of the following genes is attenuated: metJ, pykA, pykF, purU, yncA, or udhA. Methods of modifying the expression of genes in a microorganism are well known to those skilled in the art and are discussed supra and infra.

Additionally, the fermentative production of methionine by a microorganism from glucose as a main carbon source may be achieved through a combination of the above discussed modifications, for example:

the expression of the gene metJ is attenuated and the expression of a metA allele encoding for an enzyme with reduced feed-back sensitivity to S-adenosylmethionine and/or methionine (MetA*) is enhanced;

the expression of the gene metJ is attenuated; the expression of a metA allele encoding for an enzyme with reduced feed-back sensitivity to S-adenosylmethionine and/or methionine (MetA*) is enhanced; and the expression of a thrA allele encoding for an enzyme with reduced feed-back inhibition to threonine (thrA*) is enhanced;

the expression of the gene metJ is attenuated; the expression of a metA allele encoding for an enzyme with reduced feed-back sensitivity to S-adenosylmethionine and/or methionine (MetA*) is enhanced; the expression of a thrA allele encoding for an enzyme with reduced feed-back inhibition to threonine (thrA*) is enhanced; and the expression of the gene cysE is enhanced;

the expression of the gene metJ is attenuated; the expression of a metA allele encoding for an enzyme with reduced feed-back sensitivity to S-adenosylmethionine and/or methionine (MetA*) is enhanced; the expression of a thrA allele encoding for an enzyme with reduced feed-back inhibition to threonine (thrA*) is enhanced; the expression of the gene cysE is enhanced; and the expression of the genes metF and/or metH is enhanced.

In a specific embodiment of the invention, the recombinant microorganism comprises the following genetic modifications:

a) the gene pstG is overexpressed and/or does not contain the sRNA sgrS binding site and/or the gene sgrS is deleted and/or the gene sgrT is deleted and/or the gene dgsA is deleted;

b) the expression of the genes metA*, metH, cysPUWAM, cysJIH, gcvTHP, metF, serA, serB, serC, cysE, thrA* and pyc are enhanced; and c) the expression of the genes metJ, pykA, pykF, purU and yncA are attenuated.

The present invention also relates to a method of producing methionine or methionine derivatives, comprising culturing the microorganism described supra, in an appropriate culture medium comprising a fermentable source of carbon containing glucose and a source of sulphur, and recovering methionine or methionine derivatives from the culture medium.

Those skilled in the art are able to define the culture conditions for microorganisms according to the present invention. Preferably, the microorganisms are fermented at a temperature between 20° C. and 55° C., preferentially between 25° C. and 40° C., and more specifically about 37° C. for E. coli.

The fermentation is generally conducted in fermenters with an inorganic culture medium of a known, defined composition adapted to the microorganism being used, containing at least one simple carbon source, and if necessary a co-substrate necessary for the production of the metabolite. In particular, the inorganic culture medium for E. coli can be of identical or similar composition to an M9 medium (Anderson, 1946), an M63 medium (Miller, 1992) or a medium such as defined by Schaefer et al. (1999, Anal. Biochem. 270: 88-96).

The term "fermentable source of carbon" refers to any carbon source capable of being metabolized by a microorganism wherein the substrate contains at least one carbon atom. In a particular embodiment of the invention, the carbon source is derived from renewable feed-stock. Renewable feed-stock is defined as raw material required for certain industrial processes that can be regenerated within a brief delay and in sufficient amount to permit its transformation into the desired product.

According to the present invention, the source of carbon contains glucose.

After fermentation, methionine or methionine derivatives thereof may be recovered from the culture medium and, if necessary, purified. Methods of recovering and purifying a compound such as methionine and methionine derivatives from culture media are well known to those skilled in the art.

Derivatives of methionine originate from methionine transforming and/or degrading pathways. In particular these products are S-adenosyl-methionine (SAM) and N-acetyl-methionine (NAM). In particular, NAM is an easily recoverable methionine derivative that may be isolated and transformed into methionine by deacylation. Accordingly, the phrase "recovering methionine or methionine derivatives from the culture medium" refers to the action of recovering methionine, SAM, NAM and all other derivatives that may be useful.

DRAWINGS

FIG. 1: Residual glucose concentration in g/L, during cultures of strains 1 and 2. (♦): strain 1 called Ref strain; (▲): strain 2 in conditions 20/20 of IPTG concentration and (●); strain 2 in conditions 20/80 of IPTG concentration.

PROTOCOLS

Several protocols have been used to construct methionine producing strains described in the following examples.

Protocol 1

Chromosomal Modifications by Homologous Recombination and Selection of Recombinants (Datsenko & Wanner, (2000).

Allelic replacement or gene disruption in specified chromosomal locus was carried out by homologous recombination as described by Datsenko & Wanner (2000). The chloramphenicol (Cm) resistance cat, or the kanamycin (Km) resistance kan, flanked by Flp recognition sites, were amplified by PCR by using pKD3 or pKD4 plasmids as template respectively. The resulting PCR products were used to transform the recipient *E. coli* strain harbouring plasmid pKD46 that expresses the λ Red (γ, β, exo) recombinase. Antibiotic-resistant transformants were then selected and the chromosomal structure of the mutated locus was verified by PCR analysis with the appropriate primers listed in Table 1 below.

The cat resistance gene can be exchanged by the kan resistance gene by using plasmid pCP20 that carries the gene coding Flp recombinase as described by Datsenko & Wanner (2000) and the plasmid pKD4 which carries the kan gene. The pCP20 and pKD4 plasmids were introduced into the appropriated strain and the transformants were spread on LB supplemented with kanamycine at 37° C. in aim to express the flp gene and growing clones were then verified by PCR using oligonucleotides listed in Table 1.

The resistance genes were removed by using plasmid pCP20 as described by Datsenko. & Wanner (2000). Briefly, the clones harboring the pCP20 plasmid were cultivated at 37° C. on LB and then tested for loss of antibiotic resistance at 30° C. Antibiotic sensitive clones were then verified by PCR using primers listed in Table 1.

Protocol 2

Transduction of Phage P1

Chromosomal modifications were transferred to a given *E. coli* recipient strain by P1 transduction. The protocol is composed of 2 steps: (i) preparation of the phage lysate on a donor strain containing the resistance associated chromosomal modification and (ii) infection of the recipient strain by this phage lysate.

Preparation of the Phage Lysate

Inoculate 100 μl of an overnight culture of the strain MG1655 with the chromosomal modification of interest in 10 ml of LB+Cm 30 μg/ml or Km 50 μg/ml+ glucose 0.2%+CaCl$_2$ 5 mM.

Incubate 30 min at 37° C. with shaking.

Add 100 μl of P1 phage lysate prepared on the donor strain MG1655 (approx. 1×10$^9$ phage/ml).

Shake at 37° C. for 3 hours until the complete lysis of cells.

Add 200 μl of chloroform, and vortex.

Centrifuge 10 min at 4500 g to eliminate cell debris.

Transfer of supernatant to a sterile tube.

Store the lysate at 4° C.

Transduction

Centrifuge 10 min at 1500 g 5 ml of an overnight culture of the *E. coli* recipient strain cultivated in LB medium.

Suspend the cell pellet in 2.5 ml of MgSO$_4$ 10 mM, CaCl$_2$ 5 mM.

Infect 100 μl cells with 100 μl P1 phage of strain MG1655 with the modification on the chromosome (test tube) and as a control tubes 100 μl cells without P1 phage and 100 μl P1 phage without cell.

Incubate 30 min at 30° C. without shaking.

Add 100 μl sodium citrate 1 M in each tube and vortex.

Add 1 ml of LB.

Incubate 1 hour at 37° C. with shaking.

Centrifuge 3 min at 7000 rpm.

Plate on LB+Cm 30 μg/ml or Km 50 μg/ml.

Incubate at 37° C. overnight.

TABLE 1

Oligonucleotides used in the following examples.

| Oligonucleotide name | SEQ ID No | Sequence 5' → 3' |
|---|---|---|
| Ome2070-EcoRI-PlacIq-F | 1 | CCGGAATTCCATTTACGTTGACACCATCGAATGG |
| Ome2071-NheI-TT02-lacOq-R | 2 | GATTAATTGTCAACAGCTCCGTAGCTAGCAACAG ATAAAACGAAGGCCCAGTCTTTCGACTGAGCCT TTCGTTTTATTTGATGTACGTCACTGCCCGCTTTC CAGTC |
| Ome2072-GfpTurboOpt-RBS01*2- AvrII-OP01-Ptrc01-NheI-TT02-F | 3 | CGTTTTATCTGTTGCTAGCTACGGAGCTGTTGAC AATTAATCATCCGGCTCGTATAATGTGTGGAATT GTGAGCGGATAACAATTTCACCTAGGTAAGGAG GTTATAAATGGAATCTGATGAAAG |
| Ome2073-EcoRI-SfiI-PacI-TT07-R | 4 | CCAGAATTCGGCCCGGGCGGCCTTAATTAAGCAG AAAGGCCCACCCGAAG |
| Ome2115-AvrII-RBS01*2-ptsG-F | 5 | CCAAGGAAAAGCGGCCGCCCTAGGAAGGAGGTT ATAAATGTTTAAGAATGCATTTGCTAACC |
| Ome2116-BstZ17I-ptsG-R | 6 | GACGTATACTTAGTGGTTACGGATGTACTCATC |
| Ome2127-RHamont-pCC1BAC-Gt-F | 7 | CCGCTTATTATCACTTATTCAGGCGTAGCAACCA GGCGTTTAAGGGCACCAATAACTGCCTTAAAAAA ATTAGGTGGCGGTACTTGGGTCGATATCAAAGTG CATCACTTCTTCCCGTATGCCCAACTTTGTATAGA GAG |
| Ome2128-=RHaval-pCC1BAC-Gt-R | 8 | TGAAATAAGATCACTACCGGGCGTATTTTTTGAG TTATCGAGATTTTCAGGAGCTAAGGAAGCTAAAA TGTTACGCAGCAGCAACGATGTTACGCAGCAGG |

TABLE 1-continued

Oligonucleotides used in the following examples.

| Oligonucleotide name | SEQ ID No | Sequence 5' → 3' |
|---|---|---|
| | | GCAGTCGCCCTAAAACAAAGTTAGGTGGCTCAAGTATGG |
| Ome2371-DsgrS-F1 | 9 | GGACGCAAAAAGAACGCCAGTG |
| Ome2372-DsgrS-R1 | 10 | GTCATTATCCAGATCATACGTTCCCTTTTTAAACTGACGCATGGGGCACCC |
| Ome2373-DsgrS-F2 | 11 | GAAGCAAGGGGTGCCCCATGCGTCAGTTTAAAAAGGGAACGTATGATCTGGATAATGAC |
| Ome2374-DsgrS-R2 | 12 | GGAATAGGAACTAAGGAGGATATTCATATGTCAAACGTCTTTAACCTTTGCGG |
| Ome2375-DsgrS-F3 | 13 | GCATTATTTTTAACCGCAAAGGTTAAAGACGTTTGACATATGAATATCCTCCTTAGTTCCT |
| Ome2376-DsgrS-R3 | 14 | ATTGGGCTTACCTTGCAGCACGACGACGCCATTGCCGCTTATGAAGCAAAACAACCTGCGTTTATGAATTAATCCCCTTGCCCGGTCAAATGACCGGGCTTTCCGCTATCGTCCACGTCATGTAGGCTGGAGCTGCTTCG |
| Ome2378-DsgrS-Fseq | 15 | GATGGGATGGCTGGCAAAGT |
| Ome2377-DsrgS-Rseq | 16 | CGAGTTTTGCTGACATCTTCTACG |
| melBup-F | 23 | cgtaggcgccggtaccgacctcaatatcgacccagctacgc |
| melBup-R | 24 | gcttgtatacaacagataaaacgaaaggcccagtctttcgactgagcctttcgttttatttgatgcattgaaatgctcatagggtatcggtcgc |
| melBdown-F | 25 | agactgggcctttcgtttatctgttgtatacaagcttaattaacctagggcccgggcggatccgtgagtgatgtgaaagcctgacgtgg |
| melBdown-R | 26 | cgtaggcgccggtacccgaactgcactaagtaacctcttcgg |
| Km-F | 27 | tcccccggggtataccatatgaatatcctccttag |
| Km-R | 28 | gcccaagctttgtaggctggagctgcttcg |
| Ptrc01/ANR01/RBS01*2-pycre-F | 29 | cgtagttaacttaattaagagctgttgacaattaatcatccggctcgtataatgtgtggaaggtggagttatctcgagtgagatattgttgacgtaaggaggttataaaatgcccatatccaagatactcgttgccaatcg |
| pyrce-TT07-R | 30 | cgacccgggcctagggcagaaaggcccacccgaaggtgagccagtgtgagcggccgctcatccgccgtaaaccgccagcagg |
| melB-pyrce-F | 31 | gccgattttgtcgtggtggc |
| melB-pyrce-R | 32 | gcggttatccatcaggttcac |
| purUup-F | 33 | ctgaggcctatgcatggaatgcaatcgtagccacatcgc |
| purUup-R | 34 | gcttgtatacaacagataaaacgaaaggcccagtctttcgactgagcctttcgttttatttgatggctggaaaaaccttgttgagagtgtttgc |
| purUdown-F | 35 | agactgggcctttcgtttatctgttgtatacaagcttaattaacctgggccctcgcccgggcggatccggtaatcgaacgattattctttaatcgc |
| purUdown-R | 36 | ctgaggcctatgcatgcggattcgttgggaagttcaggg |
| PL1*1/RBS01*2-pyrce-F | 37 | ctctagaactagtttatctctggcggtgttgacataaataccactggcggttatactgagcacagtcgacgttaacacgcgttaaggaggttataaaatgcccatatccaagatactcgttgccaatcg |
| pyrce-TT07-R2 | 38 | tcgagcccggggcagaaaggcccacccgaaggtgagccagtacgtaagtactttaattaatcatccgccgtaaaccgccag |
| purU-pyrce-F | 39 | gcccaccagcgaaccaattg |
| purU-pyrce-R | 40 | gtaaacgtggtgccatcggg |

TABLE 1-continued

Oligonucleotides used in the following examples.

| Oligonucleotide name | SEQ ID No | Sequence 5' → 3' |
|---|---|---|
| dgsA-F | 41 | cctggcaaataacccgaatg |
| dgsA-R | 42 | cccattcagagagtggacgc |

EXAMPLE 1

Construction of Strain 2

1. Methionine Producing Strain 1

MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-ysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC (pCL1920-PgapA-pycre-TT07) has been described in patent application PCT/FR2010/052937 (published as WO2012/090021) which is incorporated as reference into this application.

2. Construction of the Strain 2

To increase the glucose import into the cell, PtsG (IIC$^{Glc}$), the glucose-specific PTS permease of the glucose phosphotransferase system was overproduced from a bacterial artificial chromosome and the use of an artificial inducible trc promoter.

The plasmid pCC1BAC-PlacIq-lacI-TT02-Ptrc01/OP01/RBS01*2-ptsG-TT07 is derived from plasmids pCC1BAC-PlacIq-lacI-TT02-Ptrc01/OP01/RBS01*2-GfpTurboOpt-TT07 (described below) and so from the bacterial artificial chromosome pCC1BAC (Epicentre).

For the construction of the plasmid pCC1BAC-PlacIq-lacI-TT02-Ptrc01/OP01/RBS01*2-GfpTurboOpt-TT07, the PlacIq-lacI-TT02-Ptrc01/OP01/RBS01*2-GfpTurboOpt-TT07 fragment was obtained by overlapping PCR. First, the PlacIq-lacI-TT02 region was amplified by PCR from plasmid pTRC99A (Stratagene) using the following oligonucleotides, Ome2070-EcoRI-PlacIq-F and Ome2071-NheI-TT02-lacIq-R, and the Ptrc01/OP01/RBS01*2-GfpTurboOpt-TT07 region was amplified by PCR from plasmid pCR4BluntTOPO-TTadc-CI857*-PlambdaR*(−35)-RBS01-GfpTurboOpt-TT07 (synthesized by Geneart and described below) using the following oligonucleotides, Ome2072-GfpTurboOpt-RBS01*2-AvrII-OP01-Ptrc01-NheI-TT02-F and Ome2073-EcoRI-SfiI-PacI-TT07-R. Then, the overlapping PCR was run by using the PlacIq-lacI-TT02 and Ptrc01/OP01/RBS01*2-GfpTurboOpt-TT07 PCR products that possess an overlapping region as matrix, and the oligonucleotides Ome2070-EcoRI-PlacIq-F and Ome2073-EcoRI-SfiI-PacI-TT07-R. The final PCR product PlacIq-lacI-TT02-Ptrc01/OP01/RBS01*2-GfpTurboOpt-TT07 was digested by EcoRI and SfiI restriction enzymes and cloned into the EcoRI/SfiI sites of the pCC1BAC vector. Recombinant plasmid was verified by DNA sequencing, giving the pCC1BAC-PlacIq-lacI-TT02-Ptrc01/OP01/RBS01*2-GfpTurboOpt-TT07 plasmid.

Ome2070-EcoRI-PlacIq-F
(SEQ ID NO 1)
ccggaattcCATTTACGTTGACACCATCGAATGG with
- lower case sequence for EcoRI restriction site and extra-bases,
- upper case sequence homologous to the PlacIq modified version of the promoter of lacI gene, carried by the pTRC99A vector (2967-2991, reference sequence on the National Center for Biotechnology Information website)

Ome2071-NheI-TT02-lacIq-R
(SEQ ID NO 2)
GATTAATTGTCAACAGCTCcgtagctagc*AACAGATAAAACGAAAGGCC*
*CAGTCTTTCGACTGAGCCTTTCGTTTTATTTGATGt*acgTCACTGCCCG
CTTTCCAGTC with
- bold upper case sequence homologous to the artificial trc promoter, Ptrc01 (Meynial-Salles et al. 2005)
- lower case sequence for NheI restriction site and extra-bases,
- upper italic case sequence for transcription terminator $T_1$ of E. coli rrnB gene (Orosz et al. 1991), reference sequence on the EcoGene website), named TT02
- upper case sequence homologous to the lacI gene (4118-4137, reference sequence on the National Center for Biotechnology Information website, or 365652-365671, reference sequence on the EcoGene website)
- underlined sequence showing the overlapping region required for the overlapping PCR step Ome2072-GfpTurboOpt-RBS01*2-AvrII-OP01-Ptrc01-NheI-TT02-F
(SEQ ID NO 3)
<u>*CGTTTTATCTGTT*</u>gctagctacgGAGCTGTTGACAATTAATCATCCCGGCTCGTATAA
TGTGTGGAATTGTGAGCGGATAACAATTtcacctagg*taaggaggttataa*ATGGAATCT
GATGAAAG with
- upper italic case sequence for transcription terminator T1 of *E. coli* rrnB gene (Orosz et al. 1991), reference sequence on the EcoGene website), named TT02
- lower case sequence for NheI or AvrII restriction site and extrabases,
- bold upper case sequence homologous to the artificial trc promoter, Ptrc01 and operator, OP01 (Meynial-Salles et al. 2005)
- bold italic lower case sequence for ribosome binding site sequence, named RBS01*2

TurboOpt-TT07 was first partially digested by AvrII and BstZ17I restriction enzymes. Then, the ptsG region was amplified by PCR from genomic DNA of *E. coli* MG1655 strain using the following oligonucleotides, Ome2115-AvrII-RBS01*2-ptsG-F and Ome2116-BstZ17I-ptsG-R and the resulting PCR product was digested by AvrII and BstZ17I restriction enzymes and cloned into the AvrII/BstZ17I sites of the pCC1BAC-PlacIq-lacI-TT02-Ptrc01/OP01/RBS01*2-GfpTurboOpt-TT07 vector. Recombinant plasmid was verified by DNA sequencing, giving the pCC1BAC-PlacIq-lacI-TT02-Ptrc01/OP01/RBS01*2-ptsG-TT07 plasmid.

Ome2115-AvrII-RBS01*2-ptsG-F
(SEQ ID NO 5)
ccaaggaaaagcggccgccctaggTAAGGAGGTTATAAATGTTTAAGAATGCATTTGCTAAcc upper case sequence homologous to a modified form of gfp gene, meaning optimized for codon usage of *E. coli*, named GfpTurboOpt
underlined sequence showing the overlapping region required for the overlapping PCR step Ome2073-EcoRI-SfiI-PacI-TT07-R
(SEQ ID NO 4)
ccagaattcggcccgggcggccttaattaa*GCAGAAAGGCCCACCCGAAG* with
- lower case sequence for EcoRI, SfiI, PacI restriction sites and extrabases
- upper italic case sequence for transcription terminator sequence T7Te (Harrington et al. 2001), named TT07
GfpTurboOpt-TT07 region present into the pCR4BluntTOPO-TTadc-CI857*-PlambdaR*(−35)-RBS01-GfpTurboOpt-TT07 plasmid, synthesized by Geneart Company (SEQ ID NO 17):

with
- lower case sequence for NotI, AvrII restriction sites and extrabases
- bold upper case sequence for ribosome binding site sequence, named RBS01*2
- upper case sequence homologous to ptsG gene (1157092-1157116, reference sequence on the EcoGene website)

Ome2116-BstZ17I-ptsG-R
(SEQ ID NO 6)
gacgtatacTTAGTGGTTACGGATGTACTCATC with
- lower case sequence for BstZ17I restriction site and extrabases
- upper case sequence homologous to ptsG gene (1158502-1158525, reference sequence on the EcoGene website)

*taaggaggttataa*atggaatctgatgaaagcggtctgcctgcaatggaaattgaatgtcgtattaccggcaccctgaatggtgttg aatttgaactggaggtggtggtgaaggtacaccggaacagggtcgtatgaccaataaaatgaaaagcaccaaaggtgcactgac catagcccgtatctgctgtctcatgttatgggctatggcattatcattaggcacctatccgagcggttatgaaaatccgtactgcatgc cattaataatggtggctataccaatacccgcattgaaaaatatgaagatggtggtgactgcatgttagattagctatcgttatgaagc cggtcgtgtgattggtgattttaaagttatgggcaccggttttccggaagatagcgtgattttttaccgataaaattattcgcagcaatgc caccgttgaacatctgcacccgatgggtgataatgatctggatggtagattacccgtaccatagcctgcgtgatggtggttattata gcagcgagtggatagccatatgcatataaaagcgccattcatccgagcattctgcagaacggtggtccgatgatgcatttcgtcgt gtggaagaagatcatagcaataccgaactgggcattgagaatatcagcatgcattaaaacaccggatgcagatgccggtgaaga ataaGTATAC<u>tcacactggctcaccacgggtgggcctactgc</u> with
- bold italic lower case sequence for ribosome binding site, named RBS01*2
- lower case sequence homologous to GfpTurbo gene (Evrogene) optimized for *E. coli*, named GfpTurboOpt
- upper case sequence for BstZ17I restriction site
- underlined case sequence for transcription terminator sequence T7Te (Harrington et al. 2001), named TT07.

To exchange the GfpTurboOpt gene by ptsG gene on the pCC1BAC-PlacIq-lacI-TT02-Ptrc01/OP01/RBS01*2-GfpTurboOpt-TT07 vector to obtain the plasmid pCC1BAC-PlacIq-lacI-TT02-Ptrc01/OP01/RBS01*2-ptsG-TT07, the pCC1BAC-PlacIq-lacI-TT02-Ptrc01/OP01/RBS01*2-Gfp- Finally, the resulting plasmid pCC1BAC-PlacIq-lacI-TT02-Ptrc01/OP01/RBS01*2-ptsG-TT07 was introduced into the strain 1 giving rise to MG1655 strain 2, MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapAmetA*11 ΔtreBC::TT02-serA-serC (pCL1920-PgapA-pycre-TT07) (pCC1BAC-PlacIq-lacI-TT02-Ptrc01/OP01/RBS01*2-ptsG-TT07).

In this construct pCC1BAC-PlacIq-lacI-TT02-Ptrc01/OP01/RBS01*2-ptsG-TT07, the natural promoter as well as the binding-site of the small RNA sgrS is replaced by a strong artificial promoter. Consequently, ptsG is overexpressed and its mRNA is no longer regulated and triggered to degradation by sgrS.

The ptsG overexpression in the strain grown under inducible conditions (+IPTG in the culture) was checked by qPCR.

EXAMPLE 2

Construction of Strain 4

1. Methionine Producing Strain 3

MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC Ptrc30-pntAB::Cm ΔuclhA (pCL1920-PgapA-pycre-TT07) has been described in patent application WO2012/055798 which is incorporated as reference into this application.

2. Construction of Strain 4

In order to overproduce PtsG in a methionine producing strain modified on its NADPH production pathway (transhydrogenases UdhA and PntAB), we had to modify the antibiotic resistance cassette of the plasmid pCC1BAC-PlacIq-lacI-TT02-Ptrc01/OP01/RBS01*2-ptsG-TT07 (described in example 1). We exchange the chloramphenicol resistance gene of the pCC1BAC-PlacIq-lacI-TT02-Ptrc01/OP01/RBS01*2-ptsG-TT07 by a gentamycin resistance gene, giving the pCC1BACVB01-PlacIq-lacI-TT02-Ptrc01/OP01/RBS01*2-ptsG-TT07 plasmid.

To proceed to this antibiotic resistance gene exchange we used a procedure based on the Red system carried by the pKD46 vector (Genebridges). For this purpose 2 oligonucleotides were used:

Ome2127-RHamont-pCC1BAC-Gt-F
(SEQ ID NO 7)
CCGCTTATTATCACTTATTCAGGCGTAGCAACCAGGCGTTTAAGGGCACCA

ATAACTGCCTTAAAAAAATTAGGTGGCGGTACTTGGGTCGATATCAAAGTG

CATCACTTCTTCCCGTATGCCCAACTTTGTATAGAGAG with
underlined upper case sequence homologous to region of pCC1BAC vector in 3' of the chloramphenicol resistance gene
upper case sequence homologous to the gentamycin resistance gene carried by the p34S-Gm vector (Dennis & Zyltra, 1998) (735-805, reference sequence on the National Center for Biotechnology Information website)
and Ome2128-RHaval-pCC1BAC-Gt-R
(SEQ ID NO 8)
TGAAATAAGATCACTACCGGGCGTATTTTTTGAGTTATCGAGATTTTCAGG

AGCTAAGGAAGCTAAAATGTTACGCAGCAGCAACGATGTTACGCAGCAGGG

CAGTCGCCCTAAAACAAAGTTAGGTGGCTCAAGTATGG with
underlined upper case sequence homologous to region of pCC1BAC vector in 5' of the chloramphenicol resistance gene
upper case homologous to the gentamycin resistance gene carried by the p34S-Gm vector (Dennis & Zyltra, 1998) (272-344, reference sequence on the National Center for Biotechnology Information website)

The oligonucleotides Ome2127-RHamont-pCC1BAC-Gt-F and Ome2128-RHaval-pCC1BAC-Gt-R were used to amplify the gentamycin resistance cassette from the plasmid p34S-Gm (Dennis & Zyltra, 1998). The PCR product obtained was then introduced by electroporation into the strain DH5 alpha (pCC1BAC-PlacIq-lacI-TT02-Ptrc01/OP01/RBS01*2-ptsG-TT07) (pKD46) in which the Red recombinase enzyme allows the homologous recombination. The gentamycin resistant and chloramphenicol sensible transformants were then selected and the insertion of the resistance cassette was verified by restriction profile analysis.

Finally, the recombinant plasmid pCC1BACVB01-PlacIq-lacI-TT02-Ptrc01/OP01/RBS01*2-ptsG-TT07 was verified by DNA sequencing and introduced into the strain 3 giving the MG1655 strain 4 MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC Ptrc30-pntAB::Cm ΔudhA (pCL1920-PgapA-pycre-TT07) (pCC1BACVB01-PlacIq-lacI-TT02-Ptrc01/OP01/RBS01*2-ptsG-TT07).

In this construct pCC1BACVB01-PlacIq-lacI-TT02-Ptrc01/OP01/RBS01*2-ptsG-TT07, the natural promoter as well as the binding-site of the small RNA sgrS is replaced by a strong artificial promoter. Consequently, ptsG is overexpressed and its mRNA is no longer regulated and triggered to degradation by sgrS.

The ptsG overexpression in the strain grown under inducible conditions (+IPTG in the culture) was checked by qPCR.

EXAMPLE 3

Construction of Strain 5

To avoid any regulation on the ptsG transcript and on the PtsG protein, we deleted the gene sgrT, that encodes a little peptide regulating PtsG activity and the part of sgrS gene which encodes for the sgrS small RNA that interferes with the mRNA of ptsG.

The genes sgrS/T are the first genes of the sgrS/T-setA operon. In order to delete sgrS/T genes without abolishing the expression of the downstream gene setA, we deleted sgrS/T and at the same time moved setA gene downstream of the promoter of the operon. For this purpose, we used the homologous recombination strategy described in Protocol 1. The *Escherichia coli* BW25113 ΔsetA::Km (pKD46) strain of the Keio mutant collection (Baba et al., 2006) was used to insert a chloramphenicol resistance cassette while deleting sgrS/T genes and restore the setA gene downstream of the operon promoter.

Specifically, the fragment "sgrR-PsgrR-PsgrS-RBSsetA-setA-FRT-Cm-FRT-leuD" (fragment 4), necessary to delete sgrS/T genes was amplified by overlapping PCR. First fragments 1, 2 and 3 which serve as matrix for the final overlapping PCR were amplified; each of these fragments possesses at least 48 nucleotides long homologous region between 3' and 5' ends which allows the overlapping PCR step. The fragment 1, "sgrR-PsgrR-PsgrS-RBSsetA-setA", was amplified from *Escherichia coli* MG1655 genomic DNA using the oligonucleotides Ome2371-DsgrS-F1 and Ome2372-DsgrS-R1; the fragment 2, "PsgrR-PsgrS-RBS-setA-setA", was amplified from *Escherichia coli* MG1655 genomic DNA using the oligonucleotides Ome2373-DsgrS-F2 and Ome2374-DsgrS-R2; the fragment 3, "FRT-Cm-FRT-leuD", was PCR amplify from the plasmid pKD3, using oligonucleotides Ome2375-DsgrS-F3 and Ome2376-DsgrS-R3. Finally, the fragment 4 was PCR amplified from a mix of fragments 1, 2 and 3 used as matrix and by using oligonucleotides Ome2371-DsgrS-F1 and Ome2376-DsgrS-R3.

Ome2371-DsgrS-F1
(SEQ ID NO 9)
GGACGCAAAAAGAAACGCCAGTG homologous to sgrR gene (76743-76765, reference sequence on the EcoGene website)

Ome2372-DsgrS-R1
(SEQ ID NO 10)
GTCATTATCCAGATCATACGTTCCCTTTTTAAACTGACGCATGGGGCACCC with
upper case sequence homologous to sgrR and sgrS promoter region (77379-77398, reference sequence on the EcoGene website)
upper bold case homologous to setA region (77637-77607, reference sequence on the EcoGene website)
underlined case sequence showing the overlapping region required for the overlapping PCR step Ome2373-DsgrS-F2
(SEQ ID NO 11)
GAAGCAAGGGGGTGCCCCATGCGTCAGTTTAAAAAGGGAACGTATGATCTG

<u>GATAATGAC</u> with
upper case sequence homologous to sgrR and sgrS promoter region (77370-77398, reference sequence on the EcoGene website)
upper bold case sequence homologous to setA region (77637-77607, reference sequence on the EcoGene website)
underlined case sequence showing the overlapping region required for the overlapping PCR step Ome2374-DsgrS-R2
(SEQ ID NO 12)
*GGAA*<u>TAGGAACTAAGGAGGATATTCATATG</u>TCAAACGTCTTTAACCTTTGC

GG with
upper italic case sequence for the amplification of the chloramphenicol resistance cassette (reference sequence in Datsenko & Wanner, 2000)
upper bold case sequence homologous to setA region (78799-78777, reference sequence on the EcoGene website)
underlined case sequence showing the overlapping region required for the overlapping PCR step Ome2375-DsgrS-F3
(SEQ ID NO 13)
GCATTATTTTTAACCGCAAAGGTTAAAGACGTTTGACATATGAATATCCTC

CTTAGTTCCT with
upper bold case sequence homologous to setA region (78764-78799, reference sequence on the EcoGene website)
upper italic case sequence for the amplification of the chloramphenicol resistance cassette (reference sequence in Datsenko & Wanner, 2000)
underlined case sequence showing the overlapping region required for the overlapping PCR step Ome2376-DsgrS-R3
(SEQ ID NO 14)
ATTGGGCTTACCTTGCAGCACGACGACGCCATTGCCGCTTATGAAGCAAAA

CAACCTGCGTTTATGAATTAATCCCCTTGCCCGGTCAAATGACCGGGCTTT

CCGCTATCGTCCACGTCATGTAGGCTGGAGCTGCTTCG with
upper case sequence homologous to setA-leuD region (78919-78800, reference sequence on the EcoGene website)
upper italic case sequence for the amplification of the chloramphenicol resistance cassette (reference sequence in Datsenko & Wanner, 2000).

The resulting PCR product, corresponding to the fragment 4, was then introduced by electroporation into the strain BW25113 ΔsetA::Km (pKD46), in which the Red recombinase enzyme allowed the homologous recombination. The chloramphenicol resistant transformants were then selected and the insertion of the resistance cassette is verified by a PCR analysis with the oligonucleotides Ome2378-DsgrS-Fseq and Ome2377-DsgrS-Rseq defined below and verified by DNA sequencing. The selected strain was called BW25113 ΔsgrS::Cm.

As sgrT open reading frame overlaps with the sgrS sequence coding for the small RNA, the deletion of sgrS results in deletion of sgrT. So, the sgrS/T deletion was called ΔsgrS.

Ome2378-DsgrS-Fseq
(SEQ ID NO 15)
GATGGGATGGCTGGCAAAGT homologous to sgrR gene (76502-76521, reference sequence on the EcoGene website)

```
Ome2377-DsgrS-Rseq
                              (SEQ ID NO 16)
CGAGTTTTGCTGACATCTTCTACG
``` homologous to leuD gene (79143-79120, reference sequence on the EcoGene website)

The sgrS/T deletion was transferred by P1 phage transduction from the BW25113 ΔsgrS::Cm strain to the strain 1. The chloramphenicol resistant transformants were then selected and the insertion of the resistance cassette was verified by a PCR analysis with the oligonucleotides Ome2378-DsgrS-Fseq and Ome2377-DsgrS-Rseq. The resulting strain was called strain 5, MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC ΔsgrS::Cm (pCL1920-PgapA-pycre-TT07).

EXAMPLE 4

Construction of Strain 6

In order to overcome the PtsG regulations in a methionine strain modified on its NADPH production pathway (transhydrogenases UdhA and PntAB), the sgrS/T genes were deleted into the strain 3.

For this purpose, the chloramphenicol resistance cassette of the ΔsgrS::Cm deletion was first exchanged by a kanamycin resistance cassette. For this, the pCP20 and pKD4 plasmids were introduced into the BW25113 ΔsgrS::Cm strain and after spreading the transformants on LB supplemented with kanamycin at 37° C., the growing clones were verified by PCR using oligonucleotides Ome2378-DsgrS-Fseq and Ome2377-DsgrS-Rseq. Then, the ΔsgrS::Km deletion was transferred by P1 phage transduction from the BW25113 ΔsgrS::Km strain to the strain 3. The kanamycin resistant transformants were then selected and the insertion of the resistance cassette was verified by a PCR analysis with the oligonucleotides Ome2378-DsgrS-Fseq and Ome2377-DsgrS-Rseq. The resulting strain was called strain 6, MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC Ptrc30-pntAB::Cm ΔudhA ΔsgrS::Km (pCL1920-PgapA-pycre-TT07).

EXAMPLE 5

Construction of Strain 7

In order to drastically increase the glucose import in strain 2 which already overexpress ptsG from pCC1BACVB01-PlacIq-lacI-TT02-Ptrc01/OP01/RBS01*2-ptsG-TT07, we deleted sgrS/T genes in that strain.

For this purpose, the ΔsgrS deletion was transferred by P1 phage transduction from the BW25113 ΔsgrS::Km strain to the strain 2. The chloramphenicol resistant transformants were then selected and the insertion of the resistance cassette was verified by a PCR analysis with the oligonucleotides Ome2378-DsgrS-Fseq and Ome2377-DsgrS-Rseq. The resulting strain was called strain 7, MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC ΔsgrS::Cm (pCL1920-PgapA-pycre-TT07) (pCC1BACVB01-PlacIq-lacI-TT02-Ptrc01/OP01/RBS01*2-ptsG-TT07).

The ptsG overexpression in the strain grown under inducible conditions (+IPTG in the culture) was checked by qPCR.

EXAMPLE 6

Construction of Strain 15

1. Strain 8

Methionine producing strain 8 has been described in patent application WO2012/055798 which is incorporated as reference into this application. The genotype of strain 8 is the following MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC.

2. Construction of the Strains 9, 10, 11 and 12

In order to overexpress the pyruvate carboxylase gene of *Rhizobium etli*, named *pycre*, a copy of this gene has been integrated twice on the chromosome at the melB and purU loci. At the melB locus, pycre gene was expressed by the addition of a synthetic Ptrc promoter sequence, an mRNA-stabilizing sequence and an optimized ribosome binding site integrated upstream of the translational start site of the pycre gene. The construct has been annotated ΔmelB::RN/Ptrc01/ARN01/RBS01*2-pycre-TT07. At the purU locus, pycre gene was expressed by the addition of the PL1*1 (mutation in the −10 box of PλL1 promoter of phage lambda) and an optimized ribosome binding site integrated upstream of the translational start site of the pycre gene. The construct has been annotated ΔpurU::RN/PL1*1/RBS01*2-pycre-TT07.

All the descriptions of the genetic integrations at different loci on the chromosome presented below are constructed according to the same method; 1) construction of the duplication vector containing upstream and downstream homologous sequences of the locus of interest, the DNA fragment and a resistance cassette 2) Integration of the modification of interest into the minimal strain (MG1655 metA*11 pKD46) by homologous recombination and 3) transduction of the modification of interest into the complex strain (MG1655 containing already several modifications).

2.1. Construction of Strains 9 and 10

To delete the melB gene and replace it by the Ptrc01/ARN01/RBS01*2-pycre-TT07 region, the homologous recombination strategy described by Datsenko & Wanner (2000) was used. This strategy allows the insertion of a chloramphenicol or a kanamycin resistance cassette but also an additional DNA, while deleting most of the genes concerned. For this purpose, the following plasmid was constructed, pUC18-ΔmelB::TT02-Ptrc01/ARN01/RBS01*2-pycre-TT07::Km. This pUC18-ΔmelB::TT02-Ptrc01/ARN01/RBS01*2-pycre-TT07::Km plasmid is derived from the pUC18 vector (Norrander et al., Gene 26 (1983), 101-106) and harbours the kanamycin resistance cassette linked to the Ptrc01/ARN01/RBS01*2-pycre-TT07 fragment, both cloned between the upstream and the downstream regions of melB.

For the construction of pUC18-ΔmelB::TT02-Ptrc01/ARN01/RBS01*2-pycre-TT07::Km, first the pUC18-ΔmelB::TT02-SMC plasmid was constructed. This plasmid carries the upstream and the downstream regions of melB which are separated by a transcriptional terminator ($T_1$ of rrnB gene of *E. coli*, named TT02) and a multiple cloning site (composed of BstZ17I, HindIII, PacI, AvrII, ApaI, SmaI, BamHI restriction sites, named SMC). This last region was PCR amplified from genomic DNA using the following oligonucleotides:

```
melBup-F
                                       (SEQ ID NO 23)
cgtaggcgccggtaccGACCTCAATATCGACCCAGCTACGC
``` with
- a region (lower case) for SfoI and KpnI restriction site and extra-bases,
- a region (upper case) homologous to the sequence (4340489-4340513) of the melB region (reference sequence on the EcoGene website).

```
melBup-R
                                       (SEQ ID NO 24)
gcttgtatacAACAGATAAAACGAAAGGCCCAGTCTTTCGACTGAGCCTT
TCGTTTTATTTGATGCATTGAAATGCTCATAGGGTATCGGGTCGC
``` with
- a region (lower case) for the BstZ17I restriction site and part of the HindIII restriction site of the multiple cloning site,
- a region (upper bold case) for the transcription terminator $T_1$ of the rrnB gene of *E. coli* (Orosz et al. 1991),
- a region (upper case) homologous to the sequence (4341377-4341406) of the melB region (reference sequence on the EcoGene website).

```
melBdown-F
                                                       (SEQ ID NO 25)
AGACTGGGCCTTTCGTTTTATCTGTTgtatacaagcttaattaacctagggcccgggcggatcc
GTGAGTGATGTGAAAGCCTGACGTGG
``` with
- a region (upper bold case) for part of the transcription terminator $T_1$ of the rrnB gene of *E. coli* (Orosz et al. 1991),
- a region (lower case) for the entire multiple cloning site,
- a region (upper case) homologous to the sequence (4342793-4342818) of the melB region (reference sequence on the EcoGene website).

```
melBdown-R
                                       (SEQ ID NO 26)
cgtaggcgccggtaccCGAACTGCACTAAGTAACCTCTTCGG
```

With
- a region (lower case) for SfoI and KpnI restriction sites and extra-bases,
- a region (upper case) homologous to the sequence (4343694-4343719) of the melB region (reference sequence on the EcoGene website).

First, the "upMelB" and "downMelB" fragments were PCR amplified from MG1655 genomic DNA using melBup-F/melBup-R and melBdown-F/melBdown-R oligonucleotides, respectively. Secondly, "upMelB-downMelB" fragment was amplified from "upMelB" and "downMelB" PCR fragments (that possess an overlapping region composed of a part of the transcription terminator $T_1$ of the rrnB gene of *E. coli* and a part of the multiple cloning site) using melBup-F/melBdown-R oligonucleotides. The "upMelB-downMelB" PCR fragment was cut with the restriction enzyme SfoI and cloned into the blunted EcoRI/HindIII sites of the pUC18 vector, giving the pUC18-ΔmelB::TT02-SMC plasmid.

Then, the kanamycin resistance cassette was PCR amplified from the pKD4 vector using the following oligonucleotides:

```
Km-F
                                       (SEQ ID NO 27)
TCCCCCGGGTATACcatatgaatatcctccttag
``` with
- a region (lower case) for the amplification of the kanamycin resistance cassette (reference sequence in Datsenko & Wanner (2000),
- a region (upper case) for SmaI and BstZ17I restriction sites and extra-bases.

```
Km-R
                                       (SEQ ID NO 28)
GCCCAAGCTTtgtaggctggagctgcttcg
``` with
- a region (lower case) for the amplification of the kanamycin resistance cassette (reference sequence in Datsenko & Wanner (2000)),
- a region (upper case) for the HindIII restriction site and extra-bases.

The PCR fragment was cut with the restriction enzymes BstZ17I and HindIII and cloned into the BstZ17I/HindIII sites of the pUC18-ΔmelB::TT02-SMC plasmid, giving the pUC18-ΔmelB::TT02-SMC::Km plasmid.

Finally, the Ptrc01/ARN01/RBS01*2-pycre-TT07 fragment was PCR amplified with primers Ptrc01/ARN01/RBS01*2-pycre-F and pycre-TT07-R from the plasmid pCL1920-PgapA-pycre-TT07, described in patent application WO2012/055798. The PCR fragment was cut with the restriction enzymes AvrII and PacI and cloned into the AvrII/PacI sites of the pUC18-ΔmelB::TT02-SMC::Km plasmid, giving the pUC18-ΔmelB::TT02-Ptrc01/ARN01/RBS01*2-pycre-TT07::Km plasmid.

Recombinant plasmids were verified by DNA sequencing.

```
Ptrc01/ARN01/RBS01*2-pycre-F
                                                  (SEQ ID NO 29)
cgtagttaacttaattaaGAGCTGTTGACAATTAATCATCCGGCTCGTATAATGTGTGG

AAGGTGGAGTTATCTCGAGTGAGATATTGTTGACGTAAGGAGGTTATAAATGCC

CATATCCAAGATACTCGTTGCCAATCG
``` with
- a region (lower case) for the PacI restriction site and extra-bases,
- a region (upper bold case) homologous to the artificial inducible trc promoter,
- a region (upper underlined case) homologous to a sequence which stabilized mRNA (Meynial-Salles et al. 2005),
- a region (upper italic case) homologous to an optimized ribosome binding site,
- a region (upper case) homologous to the start of pyc gene of Rhizobium etli (1-32).

```
pycre-TT07-R
                                                  (SEQ ID NO 30)
cgacccgggcctaggGCAGAAAGGCCCACCCGAAGGTGAGCCA GTGTGAgcggccgcTCATCCGCCGTAAACCGCCAGCAGG
``` with
- a region (lower case) for SmaI, AvrII and NotI restriction sites and extra-bases,
- a region (upper bold case) for the T7te transcriptional terminator sequence (Harrington et al. 2001), named TT07,
- a region (upper case) homologous to the end of the pyc gene of Rhizobium etli (3441-3465).

Second, the ΔmelB::TT02-Ptrc01/ARN01/RBS01*2-pycre-TT07::Km fragment was obtained by cutting the pUC18-ΔmelB::TT02-Ptrc01/ARN01/RBS01*2-pycre-TT07::Km plasmid with KpnI restriction enzyme and was then introduced by electroporation into a MG1655 metA*11 pKD46 strain, according to Protocol 1. Kanamycin resistant transformants were then selected, and the insertion of the ΔmelB::TT02-Ptrc01/ARN01/RBS01*2-pycre-TT07::Km fragment was verified by PCR analysis with the oligonucleotides melB-pycre-F and melB-pycre-R. The verified and selected strain was called MG1655 metA*11 pKD46 ΔmelB::RN/Ptrc01/ARN01/RBS01*2-pycre-TT07::Km.

```
melB-pycre-F
                                                  (SEQ ID NO 31)
gccgattttgtcgtggtggc
```
homologous to the sequence (4340168-4340187) of melB region (reference sequence on the EcoGene website)

```
melB-pycre-R
                                                  (SEQ ID NO 32)
gccggttatccatcaggttcac
```
homologous to the sequence (4344044-4344065) of the melB region (reference sequence on the EcoGene website)

Third, the ΔmelB::RN/Ptrc01/ARN01/RBS01*2-pycre-TT07::Km chromosomal modification was transduced into strain 8, with a P1 phage lysate from strain MG1655 metA*11 pKD46 ΔmelB::RN/Ptrc01/ARN01/RBS01*2-pycre-TT07::Km described above, according to Protocol 2. Kanamycin resistant transductants were selected and the presence of ΔmelB::RN/Ptrc01/ARN01/RBS01*2-pycre-TT07::Km chromosomal modification was verified by PCR with primers melB-pycre-F and melB-pycre-R. The resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC ΔmelB::RN/Ptrc01/ARN01/RBS01*2-pycre-TT07::Km was named strain 9.

The kanamycin resistance cassette was then eliminated. The pCP20 plasmid, carrying recombinase FLP acting at the FRT sites of the kanamycin resistance cassette, was introduced into strain 9. After a series of cultures at 37° C., the loss of the kanamycin resistance cassette was verified by PCR analysis with the same oligonucleotides as those used previously, melB-pycre-F/melB-pycre-R. The resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC ΔmelB::RN/Ptrc01/ARN01/RBS01*2-pycre-TT07 was named strain 10.

2.2. Construction of Strains 11 and 12

To delete the purU gene and replace it by the PL1*1/RBS01*2-pycre-TT07 region, the homologous recombination strategy described by Datsenko & Wanner (2000) was used. For this purpose, the following plasmid was constructed, pUC18-ΔpurU::TT02-PL1*1/RBS01*2-pycre-TT07::Km. This pUC18-ΔpurU::TT02-PL1*1/RBS01*2- pycre-TT07::Km plasmid is derived from the pUC18 vector (Norrander et al., Gene 26 (1983), 101-106) and harbors the kanamycin resistance cassette linked to the PL1*1/RBS01*2-pycre-TT07 fragment, both cloned between the upstream and the downstream regions of purU.

For the construction of pUC18-ΔpurU::TT02-PL1*1/RBS01*2-pycre-TT07::Km, first the pUC18-ΔpurU::TT02-SMC plasmid was constructed. This plasmid carries the upstream and the downstream regions of purU which are separated by a transcriptional terminator (T₁ of the rrnB gene of *E. coli*, named TT02) and a multiple cloning site (composed of BstZ17I, HindIII, PacI, AvrII, ApaI, SmaI, BamHI restriction sites, named SMC). This last region was PCR amplified from genomic DNA using the following oligonucleotides:

```
purUup-F
                                      (SEQ ID NO 33)
   ctgaggcctatgcatGGAATGCAATCGTAGCCACATCGC
``` with
- a region (lower case) for StuI and NsiI restriction sites and extra-bases,
- a region (upper case) homologous to the sequence (1288424-1288447) of the purU region (reference sequence on the EcoGene website).

```
purUup-R
                                      (SEQ ID NO 34)
gcttgtatacAACAGATAAAACGAAAGGCCCAGTCTTTCGACTGA

GCCTTTCGTTTTATTTGATGGCTGGAAAAACCTTGTTGAGAGTGTTTGC
``` with
- a region (lower case) for the BstZ17I restriction site and part of the HindIII restriction site of the multiple cloning site,
- a region (upper bold case) for the transcription terminator T₁ of the rrnB gene of *E. coli* (Orosz et al. 1991),
- a region (upper case) homologous to the sequence (1287849-1287877) of the purU region (reference sequence on the EcoGene website).

```
purUdown-F
                                             (SEQ ID NO 35)
AGACTGGGCCTTTCGTTTTATCTGTTgtatacaagcttaattaacctaggggccctcgcccgggcgga tccGGTAATCGAACGATTATTCTTTAATCGCC
``` with
- a region (upper bold case) for part of the transcription terminator T₁ of the rrnB gene of *E. coli* (Orosz et al. 1991),
- a region (lower case) for the entire multiple cloning site,
- a region (upper case) homologous to the sequence (1287000-1287028) of the purU region (reference sequence on the EcoGene website).

```
purUdown-R
                                      (SEQ ID NO 36)
   ctgaggcctatgcatGCGGATTCGTTGGGAAGTTCAGGG
``` with
- a region (lower case) for StuI and NsiI restriction sites and extra-bases,
- a region (upper case) homologous to the sequence (1286429-1286452) of the purU region (reference sequence on the EcoGene website).

First, the "upPurU" and "downPurU" fragments were PCR amplified from MG1655 genomic DNA using purUup-F/purUup-R and purUdown-F/purUdown-R oligonucleotides, respectively. Second, the "upPurU-downPurU" fragment was amplified from "upPurU" and "downPurU" PCR fragments (that possess an overlapping region composed of a part of the transcription terminator T₁ of the rrnB gene of *E. coli* and part of the multiple cloning site) using purUup-F/purUdown-R oligonucleotides. The "upPurU-downPurU" PCR fragment was cut with the restriction enzyme StuI and cloned into the blunted EcoRI/HindIII sites of the pUC18 vector, giving plasmid pUC18-ΔpurU::TT02-SMC.

Then, the kanamycin resistance cassette was PCR amplified from the pKD4 vector using the oligonucleotides Km-F and Km-R (described above). The PCR fragment was cut with the restriction enzymes BstZ17I and HindIII and cloned into the BstZ17I/HindIII sites of the pUC18-ΔpurU::TT02-SMC plasmid, giving plasmid pUC18-ΔpurU::TT02-SMC::Km.

Finally, the PL1*1/RBS01*2-pycre-TT07::Km fragment was PCR amplified with primers PL1*1/RBS01*2-pycre-F and pycre-TT07-R2 from plasmid pCL1920-PgapA-pycre-TT07, described in patent application WO2012/055798. The PCR fragment was cut with the restriction enzymes SpeI and SmaI and cloned into the AvrII/SmaI sites of the pUC18-ΔpurU::TT02-SMC::Km plasmid, giving the pUC18-ΔpurU::TT02-PL1*1/RBS01*2-pycre-TT07::Km plasmid. Recombinant plasmids were verified by DNA sequencing.

```
PL1*1/RBS01*2-pycre-F
                                                       (SEQ ID NO 37)
    ctctagaactagtTTATCTCTGGCGGTGTTGACATAAATACCACTGGCGGTTATAC TGAGCACAgtcgacgttaacacgcgtTAAGGAGGTTATAAATGCCCATATCCAAGATACTC

GTTGCCAATCG
``` with
- a region (lower case) for SpeI, SalI, HpaI and MluI restriction sites and extra-bases,
- a region (upper bold case) homologous to the short form of the lambda bacteriophage P_L promoter (P_{PL1} Giladi et al. 1995) and harbouring a mutation in the −10 box (G12T, underlined bold case) described in Kincade & deHaseth (1991). This promoter is called PL1*1, a region (upper italic case) homologous to an optimized ribosome binding site, a region (upper case) homologous to the 5' start of the pyc gene of *Rhizobium etli* (1-32).

pycre-TT07-R2

(SEQ ID NO 38)

tcgagcccgggGCAGAAAGGCCCACCCGAAGGTGAGCCAGtacgtaagtactttaattaaTCA

TCCGCCGTAAACCGCCAG with
 a region (lower case) for SmaI, PacI, ScaI, SnaBI restriction sites and extra-bases,
 a region (upper bold case) for the T7te transcriptional terminator sequence (Harrington et al. 2001),
 a region (upper case) homologous to the 5' end of the pyc gene of *Rhizobium etli* (3445-3465).

Second, the ΔpurU::TT02-PL1*1/RBS01*2-pycre-TT07::Km fragment was obtained by cutting the pUC18-ΔpurU::TT02-PL1*1/RBS01*2-pycre-TT07::Km plasmid with NsiI restriction enzyme and was then introduced by electroporation, according to Protocol 1, into strain MG1655 metA*11 pKD46. Kanamycin resistant transformants were then selected, and the insertion of the ΔpurU::TT02-PL1*1/RBS01*2-pycre-TT07::Km fragment was verified by a PCR analysis with the oligonucleotides purU-pycre-F and purU-pycre-R. The verified and selected strain was called MG1655 metA*11 pKD46 ΔpurU::RN/PL1*1/RBS01*2-pycre-TT07::Km.

purU-pycre-F (SEQ ID NO 39)

GCCCACCAGCGAACCAATTG homologous to the sequence (1288589-1288608) of the purU region (reference sequence on the EcoGene website)

purU-pycre-R (SEQ ID NO 40)

GTAAACGTGGTGCCATCGGG homologous to the sequence (1285868-1285887) of the purU region (reference sequence on the EcoGene website).

Third, the ΔpurU::RN/PL1*1/RBS01*2-pycre-TT07::Km chromosomal modification was transduced into strain 10, with a P1 phage lysate from strain MG1655 metA*11 pKD46 ΔpurU::RN/PL1*1/RBS01*2-pycre-TT07::Km described above, according to Protocol 2. Kanamycin resistant transductants were selected and the presence of the ΔpurU::RN/PL1*1/RBS01*2-pycre-TT07::Km chromosomal modification was verified by PCR with primers purU-pycre-F and purU-pycre-R. The resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC ΔmelB::RN/Ptrc01/ARN01/RBS01*2-pycre-TT07 ΔpurU::RN/PL1*1/RBS01*2-pycre-TT07::Km was named strain 11.

The kanamycin resistance cassette was then eliminated. The pCP20 plasmid, carrying recombinase FLP acting at the FRT sites of the kanamycin resistance cassette, was introduced into strain 11. After a series of cultures at 37° C., the loss of the kanamycin resistance cassette was verified by PCR analysis with the same oligonucleotides used previously, purU-pycre-F/purU-pycre-R. The resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC ΔmelB::RN/Ptrc01/ARN01/RBS01*2-pycre-TT07 ΔpurU::RN/PL1*1/RBS01*2-pycre-TT07 was named strain 12.

3. Construction of the Strains 13 and 14

To increase the methylene-tetrahydrofolate pool into the cell, the glycine cleavage complex encoded by the gcvTHP operon was overproduced by adding one copy of this operon on the chromosome at the yjbI locus. This additional copy of gcvTHP was expressed using an artificial inducible trc promoter and an optimized ribosome binding site, giving the ΔyjbI::RN/Ptrc01/RBS01-gcvTHP-TT07::Km chromosomal integration, described in patent application PCT/FR2012/051361.

The ΔyjbI::RN/Ptrc01/RBS01-gcvTHP-TT07::Km chromosomal modification was transduced into strain 12, with a P1 phage lysate from strain MG1655 metA*11 pKD46 ΔyjbI::RN/Ptrc01/RBS01-gcvTHP-TT07::Km, described in patent application PCT/FR2012/051361, according to Protocol 2. Kanamycin resistant transductants were selected and the presence of the ΔyjbI::RN/Ptrc01/RBS01-gcvTHP-TT07::Km chromosomal modification was verified by PCR with primers yjbI-gcvTHP-F and yjbI-gcvTHP-R, described in patent application PCT/FR2012/051361. The resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC ΔmelB::RN/Ptrc01/ARN01/RBS01*2-pycre-TT07 ΔpurU::RN/PL1*1/RBS01*2-pycre-TT07 ΔyjbI::RN/Ptrc01/RBS01-gcvTHP-TT07::Km was named strain 13.

The kanamycin resistance cassette was then eliminated. The pCP20 plasmid, carrying recombinase FLP acting at the FRT sites of the kanamycin resistance cassette, was introduced into strain 13. After a series of cultures at 37° C., the loss of the kanamycin resistance cassette was verified by PCR analysis with the same oligonucleotides used previously, yjbI-gcvTHP-F and yjbI-gcvTHP-R. The resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC ΔmelB::RN/Ptrc01/ARN01/RBS01*2-pycre-TT07 ΔpurU::RN/PL1*1/RBS01*2-pycre-TT07 ΔyjbI::RN/Ptrc01/RBS01-gcvTHP-TT07 was named strain 14.

4. Construction of the strain 15

To increase the flux into the serine pathway the plasmid pCC1BAC-TT02-Ptrc30/RBS01-serC-TT07*2-Ptrc30/RBS01-serA-TTadcca, described in the patent application PCT/FR2012/051361, was introduced into strain 14, giving the following strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC ΔmelB::RN/Ptrc01/ARN01/RBS01*2-pycre-TT07 ΔpurU::RN/PL1*1/RBS01*2-pycre-TT07 ΔyjbI::RN/Ptrc01/RBS01-gcvTHP-TT07 (pCC1BAC-TT02-Ptrc30/RBS01-serC-TT07*2-Ptrc30/RBS01-serA-TTadcca), named strain 15.

EXAMPLE 7

Construction of Strains 16 and 17

1. Construction of Strain 16

To increase the glucose import into the cell, the gene dgsA (or ink), coding for a transcriptional dual regulator that controls the expression of a number of genes encoding enzymes of the *Escherichia coli* PEP-dependent sugar phosphotransferase (PTS) system, was deleted.

To delete the dgsA gene, we used the *Escherichia coli* BW25113 ΔdgsA::Km strain of the Keio mutant collection (Baba et al., 2006). The ΔdgsA::Km deletion was transferred by P1 phage transduction (according to Protocol 2) from the BW25113 ΔdgsA::Km strain to strain 14. Kanamycin resistant transductants were selected and the presence of ΔdgsA::Km chromosomal deletion was verified by PCR with primers dgsA-F and dgsA-R defined below.

The strain retained MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC ΔmelB::RN/Ptrc01/ARN01/RBS01*2-pycre-TT07 ΔpurU::RN/PL1*1/RBS01*2-pycre-TT07 ΔyjbI::RN/Ptrc01/RBS01-gcvTHP-TT07 ΔdgsA::Km was called strain 16.

dgsA-F (SEQ ID NO 41)
CCTGGCAAATAACCCGAATG homologous to the sequence (1667067-1667086) of the dgsA region (reference sequence on the EcoGene website)

dgsA-R (SEQ ID NO 42)
CCCATTCAGAGAGTGGACGC homologous to the sequence (1664853-1664872) of the dgsA region (reference sequence on the EcoGene website).

2. Construction of Strain 17

Another way to increase the glucose import into the cell consists in overproducing PtsG (IIC$^{Glc}$), the transmembrane partner of the glucose phosphotransfer system. In order to overexpress ptsG in the background of strain 15, the following plasmid was constructed, pCC1BACVB01-PlacIq-lacI-TT02-Ptrc01/OP01/RBS01*2-ptsG-TT07-Ptrc30/RBS01-serC-TT07*2-Ptrc30/RBS01-serA-TTadcca.

The plasmid pCC1BACVB01-PlacIq-lacI-TT02-Ptrc01/OP01/RBS01*2-ptsG-TT07-Ptrc30/RBS01-serC-TT07*2-Ptrc30/RBS01-serA-TTadcca is derived from plasmid pCC1BACVB01-PlacIq-lacI-TT02-Ptrc01/OP01/RBS01*2-ptsG-TT07 (described above in Example 1, construction of strain 2) and from plasmid pCC1BAC-TT02-Ptrc30/RBS01-serC-TT07*2-Ptrc30/RBS01-serA-TTadcca, described in the patent application PCT/FR2012/051361. The Ptrc30/RBS01-serC-TT07*2-Ptrc30/RBS01-serA-TTadcca fragment was cut with the restriction enzymes SnaBI and AvrII from plasmid pCC1BAC-TT02-Ptrc30/RBS01-serC-TT07*2-Ptrc30/RBS01-serA-TTadcca and cloned into the blunted PacI site of the pCC1BACVB01-PlacIq-lacI-TT02-Ptrc01/OP01/RBS01*2-ptsG-TT07 plasmid, giving the plasmid pCC1BACVB01-PlacIq-lacI-TT02-Ptrc01/OP01/RBS01*2-ptsG-TT07-Ptrc30/RBS01-serC-TT07*2-Ptrc30/RBS01-serA-TTadcca.

Then, the plasmid pCC1BACVB01-PlacIq-lacI-TT02-Ptrc01/OP01/RBS01*2-ptsG-TT07-Ptrc30/RBS01-serC-TT07*2-Ptrc30/RBS01-serA-TTadcca was introduced into strain 16, giving the following strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC ΔmelB::RN/Ptrc01/ARN01/RBS01*2-pycre-TT07 ΔpurU::RN/PL1*1/RBS01*2-pycre-TT07 ΔyjbI::RN/Ptrc01/RBS01-gcvTHP-TT07 ΔdgsA::Km (pCC1BACVB01-PlacIq-lacI-TT02-Ptrc01/OP01/RBS01*2-ptsG-TT07-Ptrc30/RBS01-serC-TT07*2-Ptrc30/RBS01-serA-TTadcca), named strain 17.

In this plasmid pCC1BACVB01-PlacIq-lacI-TT02-Ptrc01/OP01/RBS01*2-ptsG-TT07, the natural promoter of ptsG gene as well as the binding-site of the small RNA sgrS is replaced by a strong artificial promoter (construction described in example 1 above). Consequently, ptsG is overexpressed and its mRNA is no longer regulated and triggered to degradation by sgrS.

The overexpression of the ptsG gene in strain 17 grown under inducible conditions (+IPTG in the culture) was checked by qPCR.

EXAMPLE 8

Construction of Strain 18

Strain 18 harbours a modified version of the plasmid pCC1BAC-TT02-Ptrc30/RBS01-serC-TT07*2-Ptrc30/RBS01-serA-TTadcca (which was described in the patent application PCT/FR2012/051361), meaning that we exchanged the chloramphenicol resistance gene of the pCC1BAC-TT02-Ptrc30/RBS01-serC-TT07*2-Ptrc30/RBS01-serA-TTadcca by a gentamycin resistance gene, giving plasmid pCC1BACVB01-TT02-Ptrc30/RBS01-serC-TT07*2-Ptrc30/RBS01-serA-TTadcca.

To exchange the antibiotic resistance gene of the pCC1BAC-TT02-Ptrc30/RBS01-serC-TT07*2-Ptrc30/RBS01-serA-TTadcca plasmid, we used the same procedure as described above for the construction of the pCC1BACVB01-PlacIq-lacI-TT02-Ptrc01/OP01/RBS01*2-ptsG-TT07 plasmid.

Then, the plasmid pCC1BACVB01-TT02-Ptrc30/RBS01-serC-TT07*2-Ptrc30/RBS01-serA-TTadcca was introduced into the strain 16 giving the strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 ΔtreBC::TT02-serA-serC ΔmelB::RN/Ptrc01/ARN01/RBS01*2-pycre-TT07 ΔpurU::RN/PL1*1/RBS01*2-pycre-TT07 ΔyjbI::RN/Ptrc01/RBS01-gcvTHP-TT07 ΔdgsA::Km (pCC1BACVB01-TT02-Ptrc30/RBS01-serC-TT07*2-Ptrc30/RBS01-serA-TTadcca), named strain 18.

EXAMPLE 9

Production of L-Methionine by Fermentation in Shake Flasks

Production strains were assessed in small Erlenmeyer flasks. A 5.5 mL preculture was grown at 30° C. for 21 hours in a mixed medium (10% LB medium (Sigma 25%) with 2.5 g·L$^{-1}$ glucose and 90% minimal medium PC1). It was used to inoculate a 50 mL culture of PC1 medium (Table 2) to an $OD_{600}$ of 0.2. When necessary antibiotics were added at a concentration of 50 mg·L$^{-1}$ for spectinomycin, at a concentration of 30 mg·L$^{-1}$ for chloramphenicol and at a concentration of 10 mg·L$^{-1}$ for gentamycin. IPTG was added to cultures with different concentrations indicated in each example. The temperature of the cultures was 37° C. When the culture had reached an $OD_{600}$ of 5 to 7, extracellular amino acids were quantified by HPLC after OPA/Fmoc derivatization and other relevant metabolites were analyzed using HPLC with refractometric detection (organic acids and glucose) and GC-MS after silylation. For each strain, several repetitions were made.

The methionine yield was expressed as followed:

$$Y_{met} = \frac{methionine(g)}{consumed\ glucose(g)} * 100$$

TABLE 2

| Minimal medium composition (PC1). | |
|---|---|
| Compound | Concentration (g · L$^{-1}$) |
| ZnSO$_4$•7H$_2$O | 0.0040 |
| CuCl$_2$•2H$_2$O | 0.0020 |
| MnSO$_4$•H$_2$O | 0.0200 |
| CoCl$_2$•6H$_2$O | 0.0080 |
| H$_3$BO$_3$ | 0.0010 |
| Na$_2$MoO$_4$•2H$_2$O | 0.0004 |
| MgSO$_4$•7H$_2$O | 1.00 |
| Citric acid | 6.00 |
| CaCl$_2$•2H$_2$O | 0.04 |
| K$_2$HPO$_4$ | 8.00 |
| Na$_2$HPO$_4$ | 2.00 |
| (NH$_4$)$_2$HPO$_4$ | 8.00 |
| NH$_4$Cl | 0.13 |
| NaOH 4M | Adjusted to pH 6.8 |
| FeSO$_4$•7H$_2$O | 0.04 |
| Thiamine | 0.01 |
| Glucose | 15.00 |
| Ammonium thiosulfate | 5.60 |
| Vitamin B12 | 0.01 |
| MOPS | 15.00 |

Effect of the Overexpression of ptsG on the Production of Methionine in Different Strains

TABLE 3

Yields of methionine, ketomethylvalerate and homolanthionine ($Y_{Met}$, $Y_{KMV}$, $Y_{HLA}$) in % g of product/g of glucose, produced in batch culture by strain 2. For the precise definition of the methionine/glucose yield see above. For each condition, two repetitions were made. Concentrations of HLA and KMV were measured only for one flask. IPTG (abbreviation of Isopropyl β-D-1-thiogalactopyranoside) induces transcription from the lac promoter of the plasmid pCC1BACVB01-PlacIq-lacI-TT02-Ptrc01/OP01/RBS01*2-ptsG-TT07 carried by strain 2 (see genotype in Example 1).

| IPTG concentration (µM) | $Y_{Met}$ | $Y_{KMV}$ | $Y_{HLA}$ |
|---|---|---|---|
| 0 | 9.86 ± 0.67 | 0.87 | 3.78 |
| 10 | 11.90 ± 0.17 | 0.35 | 3.55 |
| 20 | 13.32 ± 0.14 | 0.18 | 3.48 |
| 200 | 12.80 ± 0.37 | 0.13 | 3.66 |

As can be seen in table 3 the methionine production yield increases significantly upon overexpression of ptsG. The best ptsG induction is obtained with 20 µM of IPTG (checked by qPCR, data not shown) and the best production of methionine is also obtained under such conditions. Moreover, ptsG overexpression allows decreasing the ketomethylvalerate accumulation in the culture.

As information, the control strain 1 cultivated in flasks gives a yield of methionine production equivalent to the yield obtained with strain 2 without IPTG.

TABLE 4

Yields of methionine, ketomethylvalerate and homolanthionine ($Y_{Met}$, $Y_{KMV}$, $Y_{HLA}$) in % g product/g of glucose produced in batch culture by the strains 3 and 4. For the precise definition of the yields, see above. The number of repetitions is indicated in bracket. Strain 4 was cultivated with 20 μM of IPTG to induce ptsG expression.

| Strain | $Y_{Met}$ | $Y_{KMV}$ | $Y_{HLA}$ |
|---|---|---|---|
| Strain 3 (N = 27) | 9.95 ± 1.40 | 1.22 ± 0.32 | 2.87 ± 1.21 |
| Strain 4 (N = 3) | 9.86 ± 0.10 | 0.17 | 1.99 |

The overexpression of ptsG in strain 4, which has modified transhydrogenase expression (overexpression of pntAB and deletion of udhA) allows a reduction of homolanthionine and ketomethylvalerate production. In such background, the overexpression of ptsG does not enhance the methionine production yield but it clearly improves the purity of the final product.

This shows that it was not easy to predict the effect of an increased import of glucose in strains producing methionine. Effect of the Deletion of sgrS and sgrT on the Production of Methionine

TABLE 5

Methionine, ketomethylvalerate and homolanthionine yields (Ymet, YKMV, YHLA) in % g of product/g of glucose produced in batch culture by the strains 1 and 5. For the precise definition of the yields, see above. The number of repetitions is indicated in brackets.

| Strain | $Y_{met}$ | $Y_{KMV}$ | $Y_{HLA}$ |
|---|---|---|---|
| Strain 1 (N = 283) | 10.42 ± 1.87 | 1.22 ± 0.42 | 3.25 ± 0.91 |
| Strain 5 (N = 3) | 14.03 ± 0.26 | 1.92 | 3.01 |

As can be seen in table 5 above, methionine yield increases significantly upon deletion of the genes sgrS and sgrT.

SgrS inhibits translation of ptsG mRNA both directly and indirectly. The 5' end of SgrS contains a 43 amino acid open reading frame, sgrT, which regulates the activity of PtsG.

In strain 5 both genes sgrS and sgrT are deleted and the effect on the production of methionine is positive and similar to the effect obtained with an overexpression of ptsG (see Table 3).

EXAMPLE 10

Production of L-Methionine by Fermentation in Bio-Reactors with Strains 1 and 2

Strains that produced in flask substantial amounts of metabolites of interest were subsequently tested under production conditions in 2.5 L fermentors (Pierre Guerin) using a fedbatch process.

A 24 hours culture grown in 10 mL LB medium with 2.5 g·L$^{-1}$ glucose was used to inoculate a 24 hours preculture in minimal medium (B1a). These incubations were carried out in 500 mL baffled flasks containing 50 mL of minimal medium (B1a) in a rotary shaker (200 RPM). The first preculture was cultured at a temperature of 30° C., the second at a temperature of 34° C.

A third preculture step was carried out in bio-reactors (Sixfors) filled with 200 mL of minimal medium (B1b) inoculated to a biomass concentration of 1.2 g·L$^{-1}$ with 5 mL concentrated preculture. The preculture temperature was maintained constant at 34° C. and the pH was automatically adjusted to a value of 6.8 using a 10% NH$_4$OH solution. The dissolved oxygen concentration was continuously adjusted to a value of 30% of the partial air pressure saturation with air supply and/or agitation. After glucose exhaustion from the batch medium, the fedbatch was started with an initial flow rate of 0.7 mL·h$^{-1}$ and increased exponentially for 24 hours with a growth rate of 0.13 h$^{-1}$ in order to obtain a final cellular concentration of about 20 g·L$^{-1}$.

TABLE 6

Preculture batch mineral medium composition (B1a and B1b).

| Compound | B1a Concentration (g · L$^{-1}$) | B1b Concentration (g · L$^{-1}$) |
|---|---|---|
| Zn(CH$_3$COO)$_2$•2H$_2$O | 0.0130 | 0.0130 |
| CuCl$_2$•2H$_2$O | 0.0015 | 0.0015 |
| MnCl$_2$•4H$_2$O | 0.0150 | 0.0150 |
| CoCl$_2$•6H$_2$O | 0.0025 | 0.0025 |
| H$_3$BO$_3$ | 0.0030 | 0.0030 |
| Na$_2$MoO$_4$•2H$_2$O | 0.0025 | 0.0025 |
| Fe(III) citrate H$_2$O | 0.1064 | 0.1064 |
| EDTA | 0.0084 | 0.0084 |
| MgSO$_4$•7H$_2$O | 1.00 | 1.00 |
| CaCl$_2$•2H$_2$O | 0.08 | 0.08 |
| Citric acid | 1.70 | 1.70 |
| KH$_2$PO$_4$ | 4.57 | 4.57 |
| K$_2$HPO$_4$•3H$_2$O | 2.50 | 2.50 |
| (NH$_4$)$_2$HPO$_4$ | 1.10 | 1.10 |
| (NH$_4$)$_2$SO$_4$ | 4.90 | 4.90 |
| (NH$_4$)$_2$S$_2$O$_3$ | 1.00 | 1.00 |
| Thiamine | 0.01 | 0.01 |
| Vitamin B12 | 0.01 | 0.01 |
| Glucose | 30.00 | 5.00 |
| MOPS | 30.00 | 0.00 |
| NH$_4$OH 28% | Adjusted to pH 6.8 | Adjusted to pH 6.8 |

TABLE 7

Preculture fedbatch mineral medium composition (F1)

| Compound | Concentration (g · L$^{-1}$) |
|---|---|
| Zn(CH$_3$COO)$_2$•H$_2$O | 0.0104 |
| CuCl$_2$•2H$_2$O | 0.0012 |
| MnCl$_2$•4H$_2$O | 0.0120 |
| CoCl$_2$•6H$_2$O | 0.0020 |
| H$_3$BO$_3$ | 0.0024 |
| Na$_2$MoO$_4$•2H$_2$O | 0.0020 |
| Fe(III) citrate H$_2$O | 0.0424 |
| EDTA | 0.0067 |
| MgSO$_4$ | 5.00 |
| (NH$_4$)$_2$SO$_4$ | 8.30 |
| Na$_2$SO$_4$ | 8.90 |
| (NH$_4$)$_2$S$_2$O$_3$ | 24.80 |
| Thiamine | 0.01 |
| Glucose | 500.00 |
| Vitamin B12 | 0.01 |
| NH$_4$OH 28% | Adjusted to pH 6.8 |

TABLE 8

Culture batch mineral medium composition (B2).

| Compound | Concentration (g · L$^{-1}$) |
|---|---|
| Zn(CH$_3$COO)$_2$•2H$_2$O | 0.0130 |
| CuCl$_2$•2H$_2$O | 0.0015 |

TABLE 8-continued

Culture batch mineral medium composition (B2).

| Compound | Concentration (g · L$^{-1}$) |
|---|---|
| MnCl$_2$•4H$_2$O | 0.0150 |
| CoCl$_2$•6H$_2$O | 0.0025 |
| H$_3$BO$_3$ | 0.0030 |
| Na$_2$MoO$_4$•2H$_2$O | 0.0025 |
| Fe(III) citrate H$_2$O | 0.1064 |
| EDTA | 0.0084 |
| MgSO$_4$•7H$_2$O | 1.00 |
| CaCl$_2$•2H$_2$O | 0.08 |
| Citric acid | 1.70 |
| KH$_2$PO$_4$ | 2.97 |
| K$_2$HPO$_4$•3H$_2$O | 1.65 |
| (NH$_4$)$_2$HPO$_4$ | 0.72 |
| (NH$_4$)$_2$S$_2$O$_3$ | 3.74 |
| Thiamine | 0.01 |
| Vitamin B12 | 0.01 |
| Biotin | 0.10 |
| Glucose | 10 |
| NH$_4$OH 28% | Adjusted to pH 6.8 |

TABLE 9

Culture fedbatch medium composition (F2).

| Compound | Concentration (g · L$^{-1}$) |
|---|---|
| Zn(CH$_3$COO)$_2$•2H$_2$O | 0.0104 |
| CuCl$_2$•2H$_2$O | 0.0012 |
| MnCl$_2$•4H$_2$O | 0.0120 |
| CoCl$_2$•6H$_2$O | 0.0020 |
| H$_3$BO$_3$ | 0.0024 |
| Na$_2$MoO$_4$•2H$_2$O | 0.0020 |
| Fe(III) citrate H$_2$O | 0.0524 |
| EDTA | 0.0067 |
| MgSO$_4$ | 5.00 |
| (NH$_4$)$_2$S$_2$O$_3$ | 55.50 |
| Thiamine | 0.01 |
| Vitamin B12 | 0.01 |
| Biotin | 0.10 |
| Glucose | 500 |

Subsequently, the 2.5 L fermentors (Pierre Guerin) were filled with 600 mL of minimal medium (B2) and were inoculated to a biomass concentration of 2.1 g·L$^{-1}$ with a preculture volume ranging between 55 to 70 mL.

The culture temperature was maintained constant at 37° C. and pH was maintained to the working value (6.8) by automatic addition of NH$_4$OH solutions (NH$_4$OH 10% for 9 hours and 28% until the culture end). The initial agitation rate was set at 200 RPM during the batch phase and was increased up to 1000 RPM during the fedbatch phase. The initial airflow rate was set at 40 NL·h$^{-1}$ during the batch phase and was increased to 100 NL·h$^{-1}$ at the beginning of the fedbatch phase. The dissolved oxygen concentration was maintained at values between 20 and 40%, preferentially 30% saturation by increasing the agitation.

When the cell mass reached a concentration close to 5 g·L$^{-1}$, the fedbatch was started with an initial flow rate of 5 mL·h$^{-1}$. Feeding solution was injected for 14 hours with a sigmoid profile with an increasing flow rate that reached 27 mL·h$^{-1}$ after 26 hours. The precise feeding conditions were calculated by the following equation:

$$Q(t) = p1 + \frac{p2}{1 + e^{-p3(t-p4)}}.$$

where Q(t) is the feeding flow rate in mL·h$^{-1}$ for a batch volume of 600 mL.

For 14 hours, parameters were p1=1.80, p2=22.40, p3=0.27, p4=6.50 and then from 14 h to 26 hours, parameters were p1=2.00, p2=25.00, p3=0.40, p4=9.00.

After 26 hours of fedbatch, the feeding solution pump was stopped and the culture was stopped after glucose exhaustion.

Extracellular amino acids were quantified by HPLC after OPA/Fmoc derivatization and other relevant metabolites were analyzed using HPLC with refractometric detection (organic acids and glucose) and GC-MS after silylation.

TABLE 10

Methionine yields ($Y_{Met}$) in % g of methionine per g of glucose produced in fedbatch culture by strain 2 and strain 1. Strain 2 was cultivated using different concentrations of IPTG. For the definition of methionine/glucose yield see below. SD denotes the standard deviation for the yields which was calculated on the basis of several repetitions (N = number of repetitions).

| Strain | Condition | $Y_{Met}$ |
|---|---|---|
| Strain 1 | No IPTG (N = 34) | 22.06 ± 1.02 |
| Strain 2 | 20 μM IPTG in batch medium –20 μM IPTG in fed medium (N = 2) | 24.13 ± 2.31 |
| Strain 2 | 20 μM IPTG in batch medium –80 μM IPTG in fed medium (N = 1) | 23.11 |

As can be seen in table 10, independent of the IPTG concentration applied during the culture of strain 2, ptsG overexpression improves significantly the production of methionine. A constitutive overexpression of the ptsG gene in strain 2 (conditions of induction: 20 μM IPTG in batch medium-20 μM IPTG in fed medium) is the best condition to enhance methionine yield.

The induction of the expression of ptsG was checked by qPCR. Levels of ptsG mRNA were much higher in strains 2 and 3 with IPTG than in the control strain 1. See results of FIG. 1.

Upon ptsG overexpression strain 2 does not accumulate glucose during the culture nor at the end of it. On the contrary, strain 1 which has a wild type glucose import shows a strong glucose accumulation after 25 h of growth. The residual glucose concentration reaches more than 10 g/L for strain 1 and less than 3 g/L with strain 2.

Improvement of the glucose import not only improves methionine production but also improves the purity of the product.

The reactor volume was calculated by adding to the initial volume the amount of solutions added to regulate the pH and to feed the culture and by subtracting the volume used for sampling and lost by evaporation.

The fedbatch volume was followed continuously by weighing the feeding stock. The amount of injected glucose was then calculated on the basis of the injected weight, the density of the solution and the glucose concentration determined by the method of Brix ([Glucose]). Methionine yield was expressed as followed:

$$Y_{met} = \frac{Methionine_t * V_t - Methionine_0 * V_0 \times 100}{Consumed\ glucose\ e_t}$$

The maximal yield obtained during the culture was presented here for each strain. With Methionine$_0$ and Methionine, respectively the initial and final methionine concentrations and $V_0$ and $V_t$ the initial and the instant t volumes.

The consumed glucose was calculated as follows:

$$\text{fed volume}_t = \frac{\text{fed weight}_0 - \text{fed weight}_t}{\text{density fed solution}}$$

$$\text{Injected Glucose}_t = \text{fed volume}_t * [\text{Glucose}]$$

$$\text{Consumed glucose}_t = $$

$$[\text{Glucose}]_0 * V_0 + \text{Injected Glucose} - [\text{Glucose}]_{residual} * V_t$$

With $[\text{Glucose}]_0$, $[\text{Glucose}]$, $[\text{Glucose}]_{residual}$ respectively the initial, the fed and the residual glucose concentrations.

EXAMPLE 11

Production of L-Methionine by Fermentation in Bio-Reactor with Strains 15, 17 and 18

Preculture conditions were described above (Example 10).

Subsequently, 2.5 L fermentors (Pierre Guerin) were filled with 600 mL of minimal medium (B2) and were inoculated to a biomass concentration of 2.1 g·L$^{-1}$ with a preculture volume ranging between 55 to 70 mL. The final phosphate concentration in batch medium B2 was adjusted to a value comprised between 0 to 20 mM.

The culture temperature was maintained constant at 37° C. and pH was maintained to the working value (6.8) by automatic addition of NH$_4$OH solutions (NH$_4$OH 10% for 9 hours and 28% until the culture end). The initial agitation rate was set at 200 RPM during the batch phase and was increased up to 1000 RPM during the fedbatch phase. The initial airflow rate was set at 40 NL·h$^{-1}$ during the batch phase and was increased to 100 NL·h$^{-1}$ at the beginning of the fedbatch phase. The dissolved oxygen concentration was maintained at values between 20 and 40%, preferentially 30% saturation by increasing the agitation. IPTG was added to batch and fedbatch media when necessary at a final concentration of 20 µM. When necessary antibiotics were added at a concentration of 50 mg·L$^{-1}$ for kanamycin, 30 mg·L$^{-1}$ for chloramphenicol and 10 mg·L$^{-1}$ for gentamycin.

When the cell mass reached a concentration close to 5 g·L$^{-1}$, the fedbatch was started with an initial flow rate of 5 mL·h$^{-1}$. The final phosphate concentration of F2 medium was adjusted to a value comprised between 5 and 30 mM to reach a phosphate limitation during the culture. Feeding solution was injected with a sigmoid profile with an increasing flow rate that reached 27 mL·h$^{-1}$ after 26 hours. The precise feeding conditions were calculated by the equation:

$$Q(t) = p1 + \frac{p2}{1 + e^{-p3(t-p4)}}$$

where Q(t) is the feeding flow rate in mL·h$^{-1}$ for a batch volume of 600 mL with p1=1.80, p2=22.4, p3=0.27, p4=6.50. This flow rate was increased from 10 to 50%, preferentially 30% throughout the entire culture.

After 26 hours fedbatch, the feeding solution pump was stopped and the culture was stopped after glucose exhaustion.

Extracellular amino acids were quantified by HPLC after OPA/Fmoc derivatization and other relevant metabolites were analyzed using HPLC with refractometric detection (organic acids and glucose) and GC-MS after silylation.

TABLE 11

Specific glucose consumption rate (qs), maximal and final methionine yields produced in fedbatch culture by strains 17 and 18. The performances of the strains are compared to the reference strain 15. The symbol ~ indicates an increase of the parameter lower than 5% whereas the symbol + indicates an improvement greater than 5%.

| Strain | Strain 15 | Strain 17 | Strain 18 |
|---|---|---|---|
| Number of repetitions | n = 1 | n = 4 | n = 2 |
| qs (mmol · g$^{-1}$ · h$^{-1}$) | reference | + | + |
| Max meth Yield (g · g$^{-1}$) | reference | ~ | + |
| Final meth Yield (g · g$^{-1}$) | reference | + | ~ |

The specific glucose consumption rate (qs) was increased upon the deletion of the dgsA gene associated or not to the overexpression of ptsG. Moreover, the yields of methionine (both maximal and final yields) production were increased with these genetic modifications.

For the definition of methionine yields, see the example 10 above.

The specific glucose consumption rate (q$_s$) was calculated as followed:

$$q_s = \frac{\text{consumed } glc_t - \text{consumed } glc_{t-1}}{(t - (t-1)) \times [X]_t};$$

where [X] was the cellular concentration at time t.

REFERENCES

1. Plumbridge J (1998), *Mol Microbiol.* 29: 1053-1063
2. Kimata K, Inada T, Tagami H, Aiba H (1998), *Mol Microbiol.* 29: 1509-1519
3. Rungrassamee W, Liu X, Pomposiello P J (2008), *Arch Microbiol.* 190: 41-49
4. Anderson E H (1946), *Proc. Natl. Acad. Sci. USA* 32:120-128
5. Baba T, Ara T, Hasegawa M, Takai Y, Okumura Y, Baba M, Datsenko K A, Tomita M, Wanner B L, Mori H (2006), *Mol Syst Biol.* 2: 2006.0008
6. Datsenko K A, Wanner B L (2000), *Proc Natl Acad Sci USA.* 97: 6640-6645
7. Dennis J J, Zylstra G J (1998), *Appl Environ Microbiol.* 64: 2710-2715
8. Giladi H, Goldenberg D, Koby S, Oppenheim A B (1995), *FEMS Microbiol Rev.* 17: 135-140
9. Görke B, Vogel J (2008), *Genes Dev.* 22:2914-25
10. Harrington K J, Laughlin R B, Liang S (2001), *Proc Natl Acad Sci USA.* 98: 5019-5024
11. Kadner R J, Murphy G P, Stephens C M (1992), *J Gen Microbiol.* 138: 2007-2014
12. Kincade J M, deHaseth P L (1991), *Gene.* 97: 7-12
13. Kornberg H L, Reeves R E (1972), *Biochem J.* 128: 1339-1344
14. Lee A T, Cerami A (1987), *Proc Natl Acad Sci USA.* 84: 8311-8314
15. Meadow N D, Fox D K, Roseman S (1990), *Annu Rev Biochem.* 59: 497-542
16. Meynial-Salles I, Cervin M A, Soucaille P (2005), *Appl Environ Microbiol.* 71: 2140-2144
17. Miller (1992), A Short Course in Bacterial Genetics: A Laboratory Manual and Handbook for *Escherichia coli* and Related Bacteria, Cold Spring Harbor Laboratory Press, Cold Spring Harbor, N.Y.
18. Morita T, Aiba H (2007), *Proc Natl Acad Sci USA.* 104: 20149-20150
19. Natarajan A, Srienc F (1999), *Metab Eng.* 1: 320-333
20. Orosz A, Boros I, Venetianer P (1991), *Eur J Biochem.* 201: 653-659
21. Plumbridge J (2002), *Curr Opin Microbiol.* 5: 187-193
22. Prescott et al. (1999), "Microbiology" 4th Edition, WCB McGraw-Hill
23. Rohwer J M, Jensen P R, Shinohara Y, Postma P W, Westerhoff H V (1996), *Eur J Biochem.* 235:225-30
24. Sambrook et al. (1989) (2001), "Molecular Cloning: A Laboratory Manual" 2nd & 3rd Editions, Cold Spring Harbor Laboratory Press
25. Sauderson C L (1985), *Br. J Nutr.* 54: 621-633
26. Tchieu J H, Norris V, Edwards J S, Saier M H Jr (2001), *J Mol Microbiol Biotechnol.* 3: 329-346

The invention claimed is:

1. A recombinant microorganism for improved methionine production comprising:
   a) at least one modification to produce methionine from glucose as main carbon source by fermentation, and
   b) at least one modification to improve glucose import, wherein glucose import is increased compared to the microorganism without the specified modifications by overexpression of the gene ptsG encoding the PTS enzyme IICB$^{Glc}$ and deletion of the gene dgsA encoding a transcriptional regulator,
   wherein expression of at least one of the following genes is attenuated: metJ, pykA, pykF, purU, yncA, or udhA, and wherein said microorganism is *Escherichia coli*.

2. The microorganism of claim 1, wherein gene ptsG is overexpressed under control of an inducible and/or a constitutive promoter.

3. The microorganism of claim 1, wherein the gene ptsG does not contain a sequence of a binding site for a small RNA sgrS, which is SEQ ID NO: 19.

4. The microorganism of claim 1, wherein expression of gene sgrS and/or sgrT is attenuated.

5. The microorganism of claim 4, wherein the gene sgrS and/or sgrT is deleted.

6. The microorganism of claim 1, wherein expression of at least one of the following genes is enhanced: pyc, pntAB, cysP, cysU, cysW, cysA, cysMs, cysJ, cysl, cysH, gcvT, gcvH, gcvP, Ipd, serA, serB, serC, cysE, metF, metH, or thrA.

7. The microorganism of claim 6, wherein at least one gene is under control of an inducible promoter.

8. The microorganism of claim 1, wherein:
   a) gene pstG does not contain an sRNA sgrS binding site and/or gene sgrS is deleted and/or gene sgrT is deleted;
   b) expression of genes metH, cysPUWAM, cysJIH, gcvTHP, metF, serA, serB, serC, cysE, and pyc are enhanced; and
   c) expression of the genes metJ, pykA, pykF, purU and yncA are attenuated.

9. A method for fermentative production of methionine and/or a methionine derivative comprising:
   a) culturing the recombinant microorganism of claim 1 in an appropriate culture medium comprising a fermentable source of carbon comprising glucose and a source of sulphur, and
   b) recovering methionine and/or a methionine derivative from the culture medium.

10. The method of claim 9, wherein the gene ptsG does not contain a sequence of a binding site for a small RNA sgrS, which is SEQ ID NO: 19.

11. The method of claim 9, wherein expression of gene sgrS and/or sgrT is attenuated.

12. The method of claim 9, wherein gene sgrS and/or sgrT is deleted.

13. The method of claim 9, wherein expression of at least one of the following genes is enhanced: pyc, pntAB, cysP, cysU, cysW, cysA, cysts, cyst, cysI, cysH, gcvT, gcvH, gcvP, Ipd, serA, serB, serC, cysE, metF, metH, or thrA.

14. The method of claim 13, wherein at least one gene is under control of an inducible promoter.

15. The method of claim 9, wherein expression of at least one of the following genes is attenuated: metJ, pykA, pykF, purU, yncA, or udhA.

16. The method of claim 9, wherein:
d) gene pstG does not contain a sRNA sgrS binding site, which is SEQ ID NO: 19, and/or gene sgrS is deleted and/or gene sgrT is deleted;
e) expression of genes metH, cysPUWAM, cysJIH, gcvTHP, metF, serA, sere, serC, cysE, and pyc are enhanced; and
f) expression of genes metJ, pykA, pykF, purU and yncA are attenuated.

* * * * *

SEQUENCE LISTING

```
<160> NUMBER OF SEQ ID NOS: 42

<210> SEQ ID NO 1
<211> LENGTH: 34
<212> TYPE: DNA
<213> ORGANISM: Artificial Sequence
<220> FEATURE:
<223> OTHER INFORMATION: Oligonucleotide

<400> SEQUENCE: 1
ccggaattcc atttacgttg acaccatcga atgg                               34

<210> SEQ ID NO 2
<211> LENGTH: 108
<212> TYPE: DNA
<213> ORGANISM: Artificial Sequence
<220> FEATURE:
<223> OTHER INFORMATION: Oligonucleotide

<400> SEQUENCE: 2
gattaattgt caacagctcc gtagctagca acagataaaa cgaaaggccc agtctttcga    60
ctgagccttt cgttttattt gatgtacgtc actgcccgct ttccagtc                108

<210> SEQ ID NO 3
<211> LENGTH: 125
<212> TYPE: DNA
<213> ORGANISM: Artificial Sequence
<220> FEATURE:
<223> OTHER INFORMATION: Oligonucleotide

<400> SEQUENCE: 3
cgttttatct gttgctagct acggagctgt tgacaattaa tcatccggct cgtataatgt    60
gtggaattgt gagcggataa caatttcacc taggtaagga ggttatataaa ggaatctgat   120 gaaag                                                               125

<210> SEQ ID NO 4
<211> LENGTH: 50
<212> TYPE: DNA
<213> ORGANISM: Artificial Sequence
<220> FEATURE:
<223> OTHER INFORMATION: Oligonucleotide

<400> SEQUENCE: 4
ccagaattcg gcccgggcgg ccttaattaa gcagaaaggc cacccgaag                50

<210> SEQ ID NO 5
<211> LENGTH: 63
<212> TYPE: DNA
<213> ORGANISM: Artificial Sequence
<220> FEATURE:
<223> OTHER INFORMATION: Oligonucleotide

<400> SEQUENCE: 5
```

```
ccaaggaaaa gcggccgccc taggtaagga ggttataaat gtttaagaat gcatttgcta    60
acc                                                                  63

<210> SEQ ID NO 6
<211> LENGTH: 33
<212> TYPE: DNA
<213> ORGANISM: Artificial Sequence
<220> FEATURE:
<223> OTHER INFORMATION: Oligonucleotide

<400> SEQUENCE: 6
gacgtatact tagtggttac ggatgtactc atc                                 33

<210> SEQ ID NO 7
<211> LENGTH: 140
<212> TYPE: DNA
<213> ORGANISM: Artificial Sequence
<220> FEATURE:
<223> OTHER INFORMATION: Oligonucleotide

<400> SEQUENCE: 7
ccgcttatta tcacttattc aggcgtagca accaggcgtt taagggcacc aataactgcc    60
ttaaaaaaat taggtggcgg tacttgggtc gatatcaaag tgcatcactt cttcccgtat   120
gcccaacttt gtatagagag                                               140

<210> SEQ ID NO 8
<211> LENGTH: 140
<212> TYPE: DNA
<213> ORGANISM: Artificial Sequence
<220> FEATURE:
<223> OTHER INFORMATION: Oligonucleotide

<400> SEQUENCE: 8
tgaaataaga tcactaccgg gcgtattttt tgagttatcg agattttcag gagctaagga    60
agctaaaatg ttacgcagca gcaacgatgt tacgcagcag ggcagtcgcc ctaaaacaaa   120
gttaggtggc tcaagtatgg                                               140

<210> SEQ ID NO 9
<211> LENGTH: 23
<212> TYPE: DNA
<213> ORGANISM: Artificial Sequence
<220> FEATURE:
<223> OTHER INFORMATION: Oligonucleotide

<400> SEQUENCE: 9
ggacgcaaaa agaaacgcca gtg                                            23

<210> SEQ ID NO 10
<211> LENGTH: 51
<212> TYPE: DNA
<213> ORGANISM: Artificial Sequence
<220> FEATURE:
<223> OTHER INFORMATION: Oligonucleotide

<400> SEQUENCE: 10
gtcattatcc agatcatacg ttccctttt aaactgacgc atggggcacc c              51

<210> SEQ ID NO 11
<211> LENGTH: 60
<212> TYPE: DNA
<213> ORGANISM: Artificial Sequence
<220> FEATURE:
<223> OTHER INFORMATION: Oligonucleotide
```

<400> SEQUENCE: 11
gaagcaaggg ggtgccccat gcgtcagttt aaaaagggaa cgtatgatct ggataatgac    60

<210> SEQ ID NO 12
<211> LENGTH: 53
<212> TYPE: DNA
<213> ORGANISM: Artificial Sequence
<220> FEATURE:
<223> OTHER INFORMATION: Oligonucleotide

<400> SEQUENCE: 12
ggaataggaa ctaaggagga tattcatatg tcaaacgtct taacctttg cgg            53

<210> SEQ ID NO 13
<211> LENGTH: 61
<212> TYPE: DNA
<213> ORGANISM: Artificial Sequence
<220> FEATURE:
<223> OTHER INFORMATION: Oligonucleotide

<400> SEQUENCE: 13
gcattatttt taaccgcaaa ggttaaagac gtttgacata tgaatatcct ccttagttcc    60
t                                                                    61

<210> SEQ ID NO 14
<211> LENGTH: 140
<212> TYPE: DNA
<213> ORGANISM: Artificial Sequence
<220> FEATURE:
<223> OTHER INFORMATION: Oligonucleotide

<400> SEQUENCE: 14
attgggctta ccttgcagca cgacgacgcc attgccgctt atgaagcaaa acaacctgcg    60
tttatgaatt aatccccttg cccggtcaaa tgaccgggct ttccgctatc gtccacgtca   120
tgtaggctgg agctgcttcg                                               140

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide

<400> SEQUENCE: 15
gatgggatgg ctggcaaagt                                                20

<210> SEQ ID NO 16
<211> LENGTH: 24
<212> TYPE: DNA
<213> ORGANISM: Artificial Sequence
<220> FEATURE:
<223> OTHER INFORMATION: Oligonucleotide

<400> SEQUENCE: 16
cgagttttgc tgacatcttc tacg                                           24

<210> SEQ ID NO 17
<211> LENGTH: 753
<212> TYPE: DNA
<213> ORGANISM: Artificial Sequence
<220> FEATURE:
<223> OTHER INFORMATION: TT07 region

<400> SEQUENCE: 17

```
taaggaggtt ataaatggaa tctgatgaaa gcggtctgcc tgcaatggaa attgaatgtc      60
gtattaccgg caccctgaat ggtgttgaat ttgaactggt tggtggtggt gaaggtacac     120
cggaacaggg tcgtatgacc aataaaatga aagcaccaa aggtgcactg acctttagcc      180
cgtatctgct gtctcatgtt atgggctatg cttttatca ttttggcacc tatccgagcg     240
gttatgaaaa tccgtttctg catgccatta ataatggtgg ctataccaat acccgcattg     300
aaaaatatga agatggtggt gttctgcatg ttagctttag ctatcgttat gaagccggtc     360
gtgtgattgg tgattttaaa gttatgggca ccggttttcc ggaagatagc gtgattttta     420
ccgataaaat tattcgcagc aatgccaccg ttgaacatct gcacccgatg ggtgataatg     480
atctggatgg tagctttacc cgtacccttta gcctgcgtga tggtggttat tatagcagcg     540
ttgtggatag ccatatgcat tttaaaagcg ccattcatcc gagcattctg cagaacggtg     600
gtccgatgtt tgcatttcgt cgtgtggaag aagatcatag caataccgaa ctgggcattg     660
ttgaatatca gcatgccttt aaaacaccgg atgcagatgc cggtgaagaa taagtatact     720
cacactggct caccttcggg tgggcctttc tgc                                  753
```

<210> SEQ ID NO 18
<211> LENGTH: 1434
<212> TYPE: DNA
<213> ORGANISM: Escherichia coli

<400> SEQUENCE: 18

```
atgtttaaga atgcatttgc taacctgcaa aaggtcggta atcgctgat gctgccggta      60
tccgtactgc ctatcgcagg tattctgctg ggcgtcggtt ccgcgaattt cagctggctg     120
cccgccgttg tatcgcatgt tatggcagaa gcaggcggtt ccgtctttgc aaacatgcca     180
ctgatttttg cgatcggtgt cgccctcggc tttaccaata cgatggcgt atccgcgctg     240
gccgcagttg ttgcctatgg catcatggtt aaaaccatgg ccgtggttgc gccactggta     300
ctgcatttac ctgctgaaga atcgcctct aaacacctgg cggatactgg cgtactcgga     360
gggattatct ccggtgcgat cgcagcgtac atgtttaacc gtttctaccg tattaagctg     420
cctgagtatc ttggcttctt tgccggtaaa cgctttgtgc cgatcatttc tggcctggct     480
gccatctttta ctggcgttgt gctgtccttc atttggccgc cgattggttc tgcaatccag     540
accttctctc agtgggctgc ttaccagaac ccggtagttg cgtttggcat ttacggtttc     600
atcgaacgtt gcctggtacc gtttggtctg caccacatct ggaacgtacc ttttccagatg     660
cagattggtg aatacaccaa cgcagcaggt caggttttcc acggcgacat tccgcgttat     720
atggcgggtg acccgactgc gggtaaactg tctggtggct tcctgttcaa aatgtacggt     780
ctgccagctg ccgcaattgc tatctggcac tctgctaaac cagaaaaccg cgcgaaagtg     840
ggcggtatta tgatctccgc ggcgctgacc tcgttcctga ccggtatcac cgagccgatc     900
gagttctcct tcatgttcgt tgcgccgatc ctgtacatca tccacgcgat tctgcaggc      960
ctggcattcc caatctgtat tcttctgggg atgcgtgacg gtacgtcgtt ctcgcacggt    1020
ctgatcgact tcatcgttct gtctggtaac agcagcaaac tgtggctgtt cccgatcgtc    1080
ggtatcggtt atgcgattgt ttactacacc atcttccgcg tgctgattaa agcactggat    1140
ctgaaaacgc cgggtcgtga agacgcgact gaagatgcaa aagcgacagg taccagcgaa    1200
atggcaccgc tctggttgc tgcatttggt ggtaaagaaa acattactaa cctcgacgca    1260
tgtattaccc gtctgcgcgt cagcgttgct gatgtgtcta aagtggatca ggccggcctg    1320
```

```
aagaaactgg gcgcagcggg cgtagtggtt gctggttctg gtgttcaggc gattttcggt      1380
actaaatccg ataacctgaa aaccgagatg gatgagtaca tccgtaacca ctaa            1434
```

<210> SEQ ID NO 19
<211> LENGTH: 32
<212> TYPE: RNA
<213> ORGANISM: Escherichia coli

<400> SEQUENCE: 19

```
gcacccauac ucaggagcac ucucaauuau gu                                    32
```

<210> SEQ ID NO 20
<211> LENGTH: 227
<212> TYPE: DNA
<213> ORGANISM: Escherichia coli

<400> SEQUENCE: 20

```
gatgaagcaa gggggtgccc catgcgtcag ttttatcagc actatttac cgcgacagcg       60 aagttgtgct ggttgcgttg gttaagcgtc ccacaacgat taaccatgct tgaaggactg      120
atgcagtggg atgaccgcaa ttctgaaagt tgacttgcct gcatcatgtg tgactgagta      180
ttggtgtaaa atcacccgcc agcagattat acctgctggt ttttttt                   227
```

<210> SEQ ID NO 21
<211> LENGTH: 132
<212> TYPE: DNA
<213> ORGANISM: Escherichia coli

<400> SEQUENCE: 21

```
atgcgtcagt tttatcagca ctattttacc gcgacagcga agttgtgctg gttgcgttgg      60
ttaagcgtcc cacaacgatt aaccatgctt gaaggactga tgcagtggga tgaccgcaat      120
tctgaaagtt ga                                                          132
```

<210> SEQ ID NO 22
<211> LENGTH: 1221
<212> TYPE: DNA
<213> ORGANISM: Escherichia coli

<400> SEQUENCE: 22

```
gtggttgctg aaaaccagcc tgggcacatt gatcaaataa agcagaccaa cgcgggcgcg      60
gtttatcgcc tgattgatca gcttggtcca gtctcgcgta tcgatctttc ccgtctggcg      120
caactggctc ctgccagtat cactaaaatt gtccgtgaga tgctcgaagc acacctggtg      180
caagagctgg aaatcaaaga agcggggaac cgtggccgtc cggcggtggg gctggtggtt      240
gaaactgaag cctggcacta tctttctctg cgcattagtc gcggggagat tttccttgct      300
ctgcgcgatc tgagcagcaa actggtggtg aaagagtcgc aggaactggc gttaaaagat      360
gacttgccat tgctggatcg tattatttcc catatcgatc agttttttat ccgccaccag      420
aaaaaacttg agcgtctaac ttcgattgcc ataaccttgc cgggaattat tgatacggaa      480
aatggtattg tacatcgcat gccgttctac gaggatgtaa aagagatgcc gctcggcgag      540
gcgctggagc agcataccgg cgttccggtt tatattcagc atgatatcag cgcatggacg      600
atggcagagg cctgtgtttgg tgcctcacgc ggggcgcgcg atgtgattca ggtggttatc      660
gatcacaacg tggggcgggc gtcattacc gatggtcatc tgctacacgc aggcagcagt      720
agtctcgtgg aaataggcca cacacaggtc gacccgtatg ggaaacgctg ttattgcggg      780
```

```
aatcacggct gcctcgaaac catcgccagc gtggacagta ttcttgagct ggcacagctg     840
cgtcttaatc aatccatgag ctcgatgtta catggacaac cgttaaccgt ggactcattg     900
tgtcaggcgg cattgcgcgg cgatctactg gcaaaagaca tcattaccgg ggtgggcgcg     960
catgtcgggc gcattcttgc catcatggtg aatttattta acccacaaaa aatactgatt    1020
ggctcaccgt taagtaaagc ggcagatatc ctcttcccgg tcatctcaga cagcatccgt    1080
cagcaggccc ttcctgcgta tagtcagcac atcagcgttg agagtactca gttttctaac    1140
cagggcacga tggcaggcgc tgcactggta aaagacgcga tgtataacgg ttctttgttg    1200
attcgtctgt tgcagggtta a                                              1221
```

<210> SEQ ID NO 23
<211> LENGTH: 41
<212> TYPE: DNA
<213> ORGANISM: Artificial Sequence
<220> FEATURE:
<223> OTHER INFORMATION: Oligonucleotide

<400> SEQUENCE: 23

```
cgtaggcgcc ggtaccgacc tcaatatcga cccagctacg c                          41
```

<210> SEQ ID NO 24
<211> LENGTH: 95
<212> TYPE: DNA
<213> ORGANISM: Artificial Sequence
<220> FEATURE:
<223> OTHER INFORMATION: Oligonucleotide

<400> SEQUENCE: 24

```
gcttgtatac aacagataaa acgaaaggcc cagtctttcg actgagcctt tcgttttatt     60
tgatgcattg aaatgctcat agggtatcgg gtcgc                                 95
```

<210> SEQ ID NO 25
<211> LENGTH: 90
<212> TYPE: DNA
<213> ORGANISM: Artificial Sequence
<220> FEATURE:
<223> OTHER INFORMATION: Oligonucleotide

<400> SEQUENCE: 25

```
agactgggcc tttcgtttta tctgttgtat acaagcttaa ttaacctagg gcccgggcgg     60
atccgtgagt gatgtgaaag cctgacgtgg                                       90
```

<210> SEQ ID NO 26
<211> LENGTH: 42
<212> TYPE: DNA
<213> ORGANISM: Artificial Sequence
<220> FEATURE:
<223> OTHER INFORMATION: Oligonucleotide

<400> SEQUENCE: 26

```
cgtaggcgcc ggtacccgaa ctgcactaag taacctcttc gg                         42
```

<210> SEQ ID NO 27
<211> LENGTH: 35
<212> TYPE: DNA
<213> ORGANISM: Artificial Sequence
<220> FEATURE:
<223> OTHER INFORMATION: Oligonucleotide

<400> SEQUENCE: 27

```
tcccccgggg tataccatat gaatatcctc cttag                                 35
```

<210> SEQ ID NO 28
<211> LENGTH: 30
<212> TYPE: DNA
<213> ORGANISM: Artificial Sequence
<220> FEATURE:
<223> OTHER INFORMATION: Oligonucleotide

<400> SEQUENCE: 28
gcccaagctt tgtaggctgg agctgcttcg                                       30

<210> SEQ ID NO 29
<211> LENGTH: 140
<212> TYPE: DNA
<213> ORGANISM: Artificial Sequence
<220> FEATURE:
<223> OTHER INFORMATION: Oligonucleotide

<400> SEQUENCE: 29
cgtagttaac ttaattaaga gctgttgaca attaatcatc cggctcgtat aatgtgtgga     60
aggtggagtt atctcgagtg agatattgtt gacgtaagga ggttataaat gcccatatcc    120
aagatactcg ttgccaatcg                                                140

<210> SEQ ID NO 30
<211> LENGTH: 82
<212> TYPE: DNA
<213> ORGANISM: Artificial Sequence
<220> FEATURE:
<223> OTHER INFORMATION: Oligonucleotide

<400> SEQUENCE: 30
cgacccgggc ctagggcaga aaggcccacc cgaaggtgag ccagtgtgag cggccgctca     60
tccgccgtaa accgccagca gg                                              82

<210> SEQ ID NO 31
<211> LENGTH: 20
<212> TYPE: DNA
<213> ORGANISM: Artificial Sequence
<220> FEATURE:
<223> OTHER INFORMATION: Oligonucleotide

<400> SEQUENCE: 31
gccgattttg tcgtggtggc                                                 20

<210> SEQ ID NO 32
<211> LENGTH: 22
<212> TYPE: DNA
<213> ORGANISM: Artificial Sequence
<220> FEATURE:
<223> OTHER INFORMATION: Oligonucleotide

<400> SEQUENCE: 32
gccggttatc catcaggttc ac                                              22

<210> SEQ ID NO 33
<211> LENGTH: 39
<212> TYPE: DNA
<213> ORGANISM: Artificial Sequence
<220> FEATURE:
<223> OTHER INFORMATION: Oligonucleotide

<400> SEQUENCE: 33
ctgaggccta tgcatggaat gcaatcgtag ccacatcgc                            39

<210> SEQ ID NO 34
<211> LENGTH: 94
<212> TYPE: DNA
<213> ORGANISM: Artificial Sequence
<220> FEATURE:
<223> OTHER INFORMATION: Oligonucleotide

<400> SEQUENCE: 34
gcttgtatac aacagataaa acgaaaggcc cagtctttcg actgagcctt tcgttttatt    60
tgatggctgg aaaaaccttg ttgagagtgt ttgc                                94

<210> SEQ ID NO 35
<211> LENGTH: 98
<212> TYPE: DNA
<213> ORGANISM: Artificial Sequence
<220> FEATURE:
<223> OTHER INFORMATION: Oligonucleotide

<400> SEQUENCE: 35
agactgggcc tttcgtttta tctgttgtat acaagcttaa ttaacctggg ccctcgcccg    60
ggcggatccg gtaatcgaac gattattctt taatcgcc                            98

<210> SEQ ID NO 36
<211> LENGTH: 39
<212> TYPE: DNA
<213> ORGANISM: Artificial Sequence
<220> FEATURE:
<223> OTHER INFORMATION: Oligonucleotide

<400> SEQUENCE: 36
ctgaggccta tgcatgcgga ttcgttggga agttcaggg                           39

<210> SEQ ID NO 37
<211> LENGTH: 128
<212> TYPE: DNA
<213> ORGANISM: Artificial Sequence
<220> FEATURE:
<223> OTHER INFORMATION: Oligonucleotide

<400> SEQUENCE: 37
ctctagaact agtttatctc tggcggtgtt gacataaata ccactggcgg ttatactgag    60
cacagtcgac gttaacacgc gttaaggagg ttataaatgc ccatatccaa gatactcgtt   120
gccaatcg                                                            128

<210> SEQ ID NO 38
<211> LENGTH: 81
<212> TYPE: DNA
<213> ORGANISM: Artificial Sequence
<220> FEATURE:
<223> OTHER INFORMATION: Oligonucleotide

<400> SEQUENCE: 38
tcgagcccgg ggcagaaagg cccacccgaa ggtgagccag tacgtaagta ctttaattaa    60
tcatccgccg taaaccgcca g                                              81

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide

<400> SEQUENCE: 39

```
gcccaccagc gaaccaattg                                                    20

<210> SEQ ID NO 40
<211> LENGTH: 20
<212> TYPE: DNA
<213> ORGANISM: Artificial Sequence
<220> FEATURE:
<223> OTHER INFORMATION: Oligonucleotide

<400> SEQUENCE: 40
gtaaacgtgg tgccatcggg                                                    20

<210> SEQ ID NO 41
<211> LENGTH: 20
<212> TYPE: DNA
<213> ORGANISM: Artificial Sequence
<220> FEATURE:
<223> OTHER INFORMATION: Oligonucleotide

<400> SEQUENCE: 41
cctggcaaat aacccgaatg                                                    20

<210> SEQ ID NO 42
<211> LENGTH: 20
<212> TYPE: DNA
<213> ORGANISM: Artificial Sequence
<220> FEATURE:
<223> OTHER INFORMATION: Oligonucleotide

<400> SEQUENCE: 42
cccattcaga gagtggacgc                                                    20
```